United States Patent
Yun et al.

(10) Patent No.: US 11,992,350 B2
(45) Date of Patent: May 28, 2024

(54) SYSTEM AND METHOD FOR COMPACT LAMINOGRAPHY UTILIZING MICROFOCUS TRANSMISSION X-RAY SOURCE AND VARIABLE MAGNIFICATION X-RAY DETECTOR

(71) Applicant: Sigray, Inc., Concord, CA (US)

(72) Inventors: Wenbing Yun, Walnut Creek, CA (US); David John Vine, Berkeley, CA (US); Sylvia Jia Yun Lewis, San Francisco, CA (US); Sheraz Gul, San Ramon, CA (US); Janos Kirz, Berkeley, CA (US)

(73) Assignee: Sigray, Inc., Concord, CA (US)

( * ) Notice: Subject to any disclaimer, the term of this patent is extended or adjusted under 35 U.S.C. 154(b) by 0 days.

(21) Appl. No.: 18/176,760

(22) Filed: Mar. 1, 2023

(65) Prior Publication Data
US 2023/0293128 A1 Sep. 21, 2023

Related U.S. Application Data

(60) Provisional application No. 63/269,369, filed on Mar. 15, 2022.

(51) Int. Cl.
*A61B 6/42* (2024.01)

(52) U.S. Cl.
CPC .......... *A61B 6/4266* (2013.01); *A61B 6/4241* (2013.01)

(58) Field of Classification Search
CPC .......................... A61B 6/4241; A61B 6/4266
See application file for complete search history.

(56) References Cited

U.S. PATENT DOCUMENTS 2,491,224 A * 12/1949 Stava ................... A61B 6/4476
378/26
4,169,228 A 9/1979 Briska et al.
(Continued)

FOREIGN PATENT DOCUMENTS

CN 1656373 A 8/2005
CN 1829910 A 9/2006
(Continued)

OTHER PUBLICATIONS

"High performance benchtop EDXRF spectrometer with Windows®® software," published by: Rigaku Corp., Tokyo, Japan; 2017.
(Continued)

*Primary Examiner* — Blake C Riddick
(74) *Attorney, Agent, or Firm* — Knobbe, Martens, Olson & Bear, LLP

(57) ABSTRACT

An x-ray computed laminography imaging system includes a transmission x-ray source configured to generate x-rays, at least some of the x-rays propagate along an x-ray propagation axis through a region of interest of an object. The system further includes a stage assembly configured to rotate the object about a rotation axis extending through the region of interest. The system further includes at least one x-ray detector configured to intercept at least some of the x-rays propagating along the x-ray propagation axis. The at least one x-ray detector includes a scintillator, at least one optical lens, and two-dimensional pixelated imaging circuitry. The scintillator has a thickness that is substantially parallel to the x-ray propagation axis and the at least one optical lens is configured to receive visible light from the scintillator and to focus the visible light into a two-dimensional image. The at least one optical lens has a depth of focus, and the thickness
(Continued)

of the scintillator is in a range of 1 to 20 times the depth of focus.

23 Claims, 6 Drawing Sheets

(56) References Cited

U.S. PATENT DOCUMENTS

| | | | |
|---|---|---|---|
| 4,642,811 A | 2/1987 | Georgopoulos | |
| 4,926,452 A * | 5/1990 | Baker | G01N 23/043 378/22 |
| 4,945,552 A | 7/1990 | Ueda | |
| 5,081,656 A * | 1/1992 | Baker | G01N 23/044 378/58 |
| 5,097,492 A * | 3/1992 | Baker | G01N 23/043 378/22 |
| 5,132,997 A | 7/1992 | Kojima | |
| 5,173,928 A | 12/1992 | Momose et al. | |
| 5,204,887 A | 4/1993 | Hayashida et al. | |
| 5,220,591 A | 6/1993 | Ohsugi et al. | |
| 5,249,216 A | 9/1993 | Ohsugi et al. | |
| 5,259,012 A * | 11/1993 | Baker | A61B 6/027 378/22 |
| 5,280,176 A | 1/1994 | Jach et al. | |
| 5,351,278 A * | 9/1994 | Koshishiba | G01N 23/046 378/22 |
| 5,583,904 A * | 12/1996 | Adams | G01N 23/044 378/57 |
| 5,684,857 A | 11/1997 | De Bokx | |
| 5,778,039 A | 7/1998 | Hossain | |
| 5,790,628 A | 8/1998 | Ishida | |
| 5,812,629 A | 9/1998 | Clauser | |
| 5,832,052 A | 11/1998 | Hirose et al. | |
| 5,912,940 A | 6/1999 | O'Hara | |
| 5,978,440 A * | 11/1999 | Kang | G01N 23/046 378/22 |
| 6,108,398 A | 8/2000 | Mazor et al. | |
| 6,181,773 B1 | 1/2001 | Lee et al. | |
| 6,195,410 B1 | 2/2001 | Cash, Jr. | |
| 6,222,903 B1 * | 4/2001 | Kim | G01N 23/044 378/22 |
| 6,226,347 B1 | 5/2001 | Golenhofen | |
| 6,324,249 B1 * | 11/2001 | Fazzio | G01N 23/044 378/22 |
| 6,381,303 B1 | 4/2002 | Vu et al. | |
| 6,430,254 B2 | 8/2002 | Wilkins | |
| 6,442,231 B1 | 8/2002 | O'Hara | |
| 6,456,688 B1 | 9/2002 | Taguchi et al. | |
| 6,459,759 B1 * | 10/2002 | Tominaga | G01N 23/046 378/22 |
| 6,504,902 B2 | 1/2003 | Iwasaki et al. | |
| 6,512,814 B2 | 1/2003 | Yokhin et al. | |
| 6,577,704 B1 | 6/2003 | Holz | |
| 6,611,577 B1 | 8/2003 | Yamagami | |
| 6,639,968 B2 | 10/2003 | Yokhin et al. | |
| 6,711,234 B1 | 3/2004 | Loxley et al. | |
| 6,763,086 B2 | 7/2004 | Platonov | |
| 6,829,327 B1 | 12/2004 | Chen | |
| 6,895,071 B2 | 5/2005 | Yokhin et al. | |
| 6,914,723 B2 | 7/2005 | Yun et al. | |
| 6,917,472 B1 | 7/2005 | Yun et al. | |
| 6,934,359 B2 | 8/2005 | Chen | |
| 6,993,111 B1 * | 1/2006 | Annis | G01N 23/044 378/57 |
| 7,006,596 B1 | 2/2006 | Janik | |
| 7,023,955 B2 | 4/2006 | Chen et al. | |
| 7,095,822 B1 | 8/2006 | Yun | |
| 7,119,953 B2 | 10/2006 | Yun et al. | |
| 7,120,228 B2 | 10/2006 | Yokhin et al. | |
| 7,130,375 B1 * | 10/2006 | Yun | G01N 23/044 378/208 |
| 7,180,979 B2 | 2/2007 | Momose | |
| 7,183,547 B2 | 2/2007 | Yun et al. | |
| 7,187,751 B2 | 3/2007 | Kawahara et al. | |
| 7,215,736 B1 | 5/2007 | Wang et al. | |
| 7,218,703 B2 | 5/2007 | Yada et al. | |
| 7,221,731 B2 | 5/2007 | Yada et al. | |
| 7,221,732 B1 * | 5/2007 | Annis | G01N 23/044 378/57 |
| 7,245,696 B2 | 7/2007 | Yun et al. | |
| 7,258,485 B2 | 8/2007 | Nakano et al. | |
| 7,268,945 B2 | 9/2007 | Yun et al. | |
| 7,388,208 B2 * | 6/2008 | Deych | G01T 1/2985 250/370.11 |
| 7,388,942 B2 | 6/2008 | Wang et al. | |
| 7,394,890 B1 | 7/2008 | Wang et al. | |
| 7,400,704 B1 | 7/2008 | Yun et al. | |
| 7,406,151 B1 | 7/2008 | Yun | |
| 7,414,787 B2 | 8/2008 | Yun et al. | |
| 7,453,560 B2 | 11/2008 | Miyake | |
| 7,463,712 B2 | 12/2008 | Zhu et al. | |
| 7,486,770 B2 | 2/2009 | Baumann | |
| 7,492,871 B2 | 2/2009 | Popescu | |
| 7,499,521 B2 | 3/2009 | Wang et al. | |
| 7,515,684 B2 | 4/2009 | Gibson et al. | |
| 7,522,698 B2 | 4/2009 | Popescu | |
| 7,522,708 B2 | 4/2009 | Heismann | |
| 7,532,704 B2 | 5/2009 | Hempel | |
| 7,551,719 B2 | 6/2009 | Yokhin et al. | |
| 7,551,722 B2 | 6/2009 | Ohshima et al. | |
| 7,561,662 B2 | 7/2009 | Wang et al. | |
| 7,564,941 B2 | 7/2009 | Baumann | |
| 7,639,786 B2 | 12/2009 | Baumann | |
| 7,646,843 B2 | 1/2010 | Popescu et al. | |
| 7,653,177 B2 | 1/2010 | Baumann et al. | |
| 7,680,243 B2 | 3/2010 | Yokhin et al. | |
| 7,787,588 B1 | 8/2010 | Yun et al. | |
| 7,796,725 B1 | 9/2010 | Yun et al. | |
| 7,796,726 B1 | 9/2010 | Gendreau et al. | |
| 7,809,113 B2 | 10/2010 | Aoki et al. | |
| 7,813,475 B1 | 10/2010 | Wu et al. | |
| 7,817,777 B2 | 10/2010 | Baumann et al. | |
| 7,848,483 B2 | 12/2010 | Platonov | |
| 7,860,211 B1 * | 12/2010 | Annis | G01N 23/044 378/57 |
| 7,864,922 B2 | 1/2011 | Kawabe | |
| 7,889,838 B2 | 2/2011 | David et al. | |
| 7,899,154 B2 | 3/2011 | Chen et al. | |
| 7,920,676 B2 | 4/2011 | Yun et al. | |
| 7,924,973 B2 | 4/2011 | Kottler et al. | |
| 7,945,018 B2 | 5/2011 | Heismann | |
| 7,949,092 B2 | 5/2011 | Brons | |
| 7,949,095 B2 | 5/2011 | Ning | |
| 7,974,379 B1 | 7/2011 | Case et al. | |
| 7,983,381 B2 | 7/2011 | David et al. | |
| 8,005,185 B2 | 8/2011 | Popescu | |
| 8,009,796 B2 | 8/2011 | Popescu | |
| 8,009,797 B2 | 8/2011 | Ouchi | |
| 8,041,004 B2 | 10/2011 | David | |
| 8,058,621 B2 | 11/2011 | Kommareddy | |
| 8,068,579 B1 | 11/2011 | Yun et al. | |
| 8,073,099 B2 | 12/2011 | Niu et al. | |
| 8,139,711 B2 | 3/2012 | Takahashi | |
| 8,165,270 B2 | 4/2012 | David et al. | |
| 8,184,771 B2 | 5/2012 | Murakoshi | |
| 8,233,587 B2 | 7/2012 | Sato | |
| 8,243,879 B2 | 8/2012 | Itoh et al. | |
| 8,306,183 B2 | 11/2012 | Koehler | |
| 8,351,570 B2 | 1/2013 | Nakamura | |
| 8,353,628 B1 | 1/2013 | Yun et al. | |
| 8,374,309 B2 | 2/2013 | Donath | |
| 8,451,975 B2 | 5/2013 | Tada | |
| 8,513,603 B1 | 8/2013 | Lederman et al. | |
| 8,559,594 B2 | 10/2013 | Ouchi | |
| 8,559,597 B2 | 10/2013 | Chen et al. | |
| 8,565,371 B2 | 10/2013 | Bredno | |
| 8,591,108 B2 | 11/2013 | Tada | |
| 8,602,648 B1 | 12/2013 | Jacobsen et al. | |
| 8,632,247 B2 | 1/2014 | Ishii | |
| 8,755,487 B2 | 6/2014 | Kaneko | |
| 8,767,915 B2 | 7/2014 | Stutman | |
| 8,767,916 B2 | 7/2014 | Hashimoto | |
| 8,781,069 B2 | 7/2014 | Murakoshi | |

(56) References Cited

U.S. PATENT DOCUMENTS

| | | |
|---|---|---|
| 8,824,629 B2 | 9/2014 | Ishii |
| 8,855,265 B2 | 10/2014 | Engel |
| 8,859,977 B2 | 10/2014 | Kondoh |
| 8,908,824 B2 | 12/2014 | Kondoh |
| 8,972,191 B2 | 3/2015 | Stampanoni et al. |
| 8,989,474 B2 | 3/2015 | Kido et al. |
| 9,001,967 B2 | 4/2015 | Baturin |
| 9,016,943 B2 | 4/2015 | Jacobsen et al. |
| 9,025,725 B2 | 5/2015 | Kiyohara et al. |
| 9,031,201 B2 | 5/2015 | Sato |
| 9,036,773 B2 | 5/2015 | David et al. |
| 9,063,055 B2 | 6/2015 | Ouchi |
| 9,086,536 B2 | 7/2015 | Pang et al. |
| 9,129,715 B2 | 9/2015 | Adler et al. |
| 9,222,899 B2 | 12/2015 | Yamaguchi |
| 9,230,703 B2 | 1/2016 | Mohr et al. |
| 9,234,856 B2 | 1/2016 | Mukaide |
| 9,291,578 B2 | 3/2016 | Adler |
| 9,329,141 B2 | 5/2016 | Stutman |
| 9,357,975 B2 | 6/2016 | Baturin |
| 9,439,613 B2 | 9/2016 | Stutman |
| 9,448,190 B2 | 9/2016 | Yun et al. |
| 9,453,803 B2 | 9/2016 | Radicke |
| 9,480,447 B2 | 11/2016 | Mohr et al. |
| 9,486,175 B2 | 11/2016 | Fredenberg et al. |
| 9,494,534 B2 | 11/2016 | Baturin |
| 9,532,760 B2 | 1/2017 | Anton et al. |
| 9,551,677 B2 | 1/2017 | Mazor et al. |
| 9,557,280 B2 | 1/2017 | Pfeiffer et al. |
| 9,570,265 B1 | 2/2017 | Yun et al. |
| 9,588,066 B2 | 3/2017 | Pois et al. |
| 9,594,036 B2 | 3/2017 | Yun et al. |
| 9,632,040 B2 | 4/2017 | Stutman |
| 9,700,267 B2 | 7/2017 | Baturin et al. |
| 9,719,947 B2 | 8/2017 | Yun et al. |
| 9,748,012 B2 | 8/2017 | Yokoyama |
| 9,757,081 B2 | 9/2017 | Proksa |
| 9,761,021 B2 | 9/2017 | Koehler |
| 9,770,215 B2 | 9/2017 | Souchay et al. |
| 9,778,213 B2 | 10/2017 | Bakeman et al. |
| 9,823,203 B2 | 11/2017 | Yun et al. |
| 9,826,949 B2 | 11/2017 | Ning |
| 9,861,330 B2 | 1/2018 | Rossl |
| 9,874,531 B2 | 1/2018 | Yun et al. |
| 9,881,710 B2 | 1/2018 | Roessl |
| 9,916,655 B2 | 3/2018 | Sampanoni |
| 10,028,716 B2 | 7/2018 | Rossl |
| 10,045,753 B2 | 8/2018 | Teshima |
| 10,074,451 B2 | 9/2018 | Kottler et al. |
| 10,076,297 B2 | 9/2018 | Bauer |
| 10,085,701 B2 | 10/2018 | Hoshino |
| 10,141,081 B2 | 11/2018 | Preusche |
| 10,151,713 B2 | 12/2018 | Wu et al. |
| 10,153,061 B2 | 12/2018 | Yokoyama |
| 10,153,062 B2 | 12/2018 | Gall et al. |
| 10,247,683 B2 | 4/2019 | Yun et al. |
| 10,267,752 B2 | 4/2019 | Zhang et al. |
| 10,267,753 B2 | 4/2019 | Zhang et al. |
| 10,295,485 B2 | 5/2019 | Yun et al. |
| 10,304,580 B2 | 5/2019 | Yun et al. |
| 10,349,908 B2 | 7/2019 | Yun et al. |
| 10,352,695 B2 | 7/2019 | Dziura et al. |
| 10,352,880 B2 | 7/2019 | Yun et al. |
| 10,401,309 B2 | 9/2019 | Yun et al. |
| 10,416,099 B2 | 9/2019 | Yun et al. |
| 10,466,185 B2 | 11/2019 | Yun et al. |
| 10,473,598 B2 | 11/2019 | Ogata et al. |
| 10,485,492 B2 | 11/2019 | Koehler et al. |
| 10,514,345 B2 | 12/2019 | Ogata et al. |
| 10,514,346 B2 | 12/2019 | Sako |
| 10,568,588 B2 | 2/2020 | Koehler et al. |
| 10,578,566 B2 | 3/2020 | Yun et al. |
| 10,634,628 B2 | 4/2020 | Kasper et al. |
| 10,653,376 B2 | 5/2020 | Yun et al. |
| 10,697,902 B2 | 6/2020 | Sharma et al. |
| 10,782,252 B2 | 9/2020 | Gateshki et al. |
| 10,794,845 B2 | 10/2020 | Filsinger |
| 10,895,541 B2 | 1/2021 | Shchegrov et al. |
| 10,962,491 B2 | 3/2021 | Yun et al. |
| 10,976,270 B2 | 4/2021 | Wormington |
| 10,989,819 B2 | 4/2021 | Wieczorek et al. |
| 11,054,375 B2 | 6/2021 | Seidler et al. |
| 11,175,243 B1 | 11/2021 | Yun et al. |
| 11,215,572 B2 | 1/2022 | Yun et al. |
| 11,549,895 B2 | 1/2023 | Yun et al. |
| 11,686,692 B2 | 6/2023 | Vine et al. |
| 2001/0046276 A1 | 11/2001 | Schneider et al. |
| 2002/0015520 A1* | 2/2002 | Roder ................ G01N 23/044 382/147 |
| 2002/0080913 A1* | 6/2002 | Roder ................ G01N 23/044 378/57 |
| 2002/0150208 A1 | 10/2002 | Yohkin et al. |
| 2003/0035576 A1* | 2/2003 | Roder ................ G06T 7/0004 382/145 |
| 2003/0072413 A1 | 4/2003 | Yokhin et al. |
| 2003/0081718 A1* | 5/2003 | Oikawa ................ A61B 6/032 378/21 |
| 2003/0142781 A1 | 7/2003 | Kawahara |
| 2003/0223536 A1 | 12/2003 | Yun et al. |
| 2004/0028186 A1 | 2/2004 | Yokhin et al. |
| 2004/0047446 A1 | 3/2004 | Platonov |
| 2004/0101110 A1* | 5/2004 | Eppler ................ H05G 1/52 378/207 |
| 2004/0114712 A1* | 6/2004 | Eppler ................ H01J 35/112 378/25 |
| 2004/0114713 A1* | 6/2004 | Bohn ................ G01N 23/044 378/34 |
| 2005/0074088 A1* | 4/2005 | Ichihara ................ G01N 23/046 378/58 |
| 2005/0087699 A1 | 4/2005 | Miyake |
| 2005/0226376 A1* | 10/2005 | Yun ................ G01T 1/202 378/62 |
| 2005/0265517 A1* | 12/2005 | Gary ................ A61B 6/4035 378/21 |
| 2005/0282300 A1 | 12/2005 | Yun et al. |
| 2005/0286680 A1 | 12/2005 | Momose |
| 2006/0056585 A1* | 3/2006 | Georgeson ................ G01N 23/083 378/57 |
| 2006/0062350 A1 | 3/2006 | Yokhin |
| 2006/0088139 A1 | 4/2006 | Nankano et al. |
| 2006/0169893 A1 | 8/2006 | Lee et al. |
| 2006/0182322 A1 | 8/2006 | Bernhardt et al. |
| 2006/0192129 A1* | 8/2006 | Yun ................ G01T 1/2002 250/370.11 |
| 2007/0064869 A1* | 3/2007 | Albert ................ G01N 23/044 378/57 |
| 2007/0108387 A1 | 5/2007 | Yun et al. |
| 2007/0183563 A1 | 8/2007 | Baumann |
| 2007/0183579 A1 | 8/2007 | Baumann et al. |
| 2007/0189449 A1 | 8/2007 | Baumann |
| 2007/0248215 A1 | 10/2007 | Ohshima et al. |
| 2007/0285643 A1 | 12/2007 | Wedowski et al. |
| 2008/0043908 A1 | 2/2008 | Teramoto et al. |
| 2008/0084966 A1 | 4/2008 | Aoki et al. |
| 2008/0159475 A1 | 7/2008 | Mazor et al. |
| 2008/0170662 A1 | 7/2008 | Reinhold |
| 2008/0181363 A1 | 7/2008 | Fenter et al. |
| 2008/0273662 A1 | 11/2008 | Yun |
| 2008/0298538 A1* | 12/2008 | Wen ................ G01N 23/044 378/11 |
| 2009/0052619 A1 | 2/2009 | Endoh |
| 2009/0092227 A1 | 4/2009 | David |
| 2009/0154640 A1 | 6/2009 | Baumann et al. |
| 2009/0316857 A1 | 12/2009 | David et al. |
| 2010/0061508 A1 | 3/2010 | Takahashi |
| 2010/0091947 A1 | 4/2010 | Niu |
| 2010/0096558 A1* | 4/2010 | Danielsson ................ G01T 1/00 250/370.11 |
| 2010/0142672 A1* | 6/2010 | Crowley ................ G01N 23/044 378/57 |
| 2010/0230605 A1* | 9/2010 | Partouche-Sebban .... G01T 1/20 250/484.2 |
| 2010/0246765 A1 | 9/2010 | Murakoshi |

(56) References Cited

U.S. PATENT DOCUMENTS

| | | |
|---|---|---|
| 2010/0260315 A1 | 10/2010 | Sato et al. |
| 2010/0284513 A1 | 11/2010 | Kawabe |
| 2010/0329532 A1 | 12/2010 | Masuda et al. |
| 2011/0085641 A1 | 4/2011 | Okunuki et al. |
| 2011/0222650 A1* | 9/2011 | Muenker .............. G01N 23/046 378/20 |
| 2011/0243302 A1 | 10/2011 | Murakoshi |
| 2011/0261164 A1* | 10/2011 | Olesen ................. G01N 17/00 382/128 |
| 2011/0261924 A1* | 10/2011 | Bredno ................ A61B 6/032 378/9 |
| 2011/0268252 A1 | 11/2011 | Ozawa et al. |
| 2011/0299653 A1* | 12/2011 | Mishra ................ G01N 23/046 378/22 |
| 2012/0041679 A1 | 2/2012 | Stampanoni |
| 2012/0224670 A1 | 9/2012 | Kiyohara et al. |
| 2012/0228475 A1 | 9/2012 | Pang et al. |
| 2012/0257715 A1* | 10/2012 | Kobayashi ........... A61B 6/5282 250/366 |
| 2012/0288059 A1* | 11/2012 | Johnson ............... G01V 5/22 378/53 |
| 2013/0011040 A1 | 1/2013 | Kido et al. |
| 2013/0039460 A1 | 2/2013 | Levy |
| 2013/0108012 A1 | 5/2013 | Sato |
| 2013/0108022 A1 | 5/2013 | Kugland et al. |
| 2013/0202084 A1 | 8/2013 | Piorek et al. |
| 2013/0251100 A1 | 9/2013 | Sasaki et al. |
| 2013/0308112 A1 | 11/2013 | Clube et al. |
| 2014/0016744 A1* | 1/2014 | Muenker ............... G01N 23/04 378/42 |
| 2014/0023973 A1 | 1/2014 | Marconi et al. |
| 2014/0037052 A1 | 2/2014 | Adler |
| 2014/0064445 A1 | 3/2014 | Adler |
| 2014/0072104 A1 | 3/2014 | Jacobsen et al. |
| 2014/0105353 A1 | 4/2014 | Pfeiffer et al. |
| 2014/0105363 A1 | 4/2014 | Chen et al. |
| 2014/0112440 A1 | 4/2014 | David et al. |
| 2014/0146945 A1 | 5/2014 | Fredenberg et al. |
| 2014/0153692 A1 | 6/2014 | Larkin et al. |
| 2014/0205057 A1 | 7/2014 | Koehler et al. |
| 2014/0226785 A1 | 8/2014 | Stutman et al. |
| 2014/0270060 A1 | 9/2014 | Date et al. |
| 2014/0301528 A1* | 10/2014 | La Riviere ......... G01N 23/2251 378/62 |
| 2015/0023472 A1 | 1/2015 | Schmitt et al. |
| 2015/0030126 A1 | 1/2015 | Radicke |
| 2015/0043713 A1 | 2/2015 | Chen |
| 2015/0049860 A1 | 2/2015 | Das |
| 2015/0051877 A1 | 2/2015 | Bakeman et al. |
| 2015/0055743 A1 | 2/2015 | Vedantham et al. |
| 2015/0055745 A1 | 2/2015 | Holzner et al. |
| 2015/0071402 A1 | 3/2015 | Handa |
| 2015/0115161 A1* | 4/2015 | Bagamery ............ G06F 30/00 250/361 R |
| 2015/0117599 A1 | 4/2015 | Yun et al. |
| 2015/0146847 A1 | 5/2015 | Liu |
| 2015/0160354 A1* | 6/2015 | Mertens .............. G01N 23/046 378/9 |
| 2015/0243397 A1 | 8/2015 | Yun et al. |
| 2015/0247811 A1 | 9/2015 | Yun et al. |
| 2015/0260663 A1 | 9/2015 | Yun et al. |
| 2015/0270023 A1 | 9/2015 | Adler |
| 2015/0323474 A1 | 11/2015 | Case et al. |
| 2015/0323478 A1 | 11/2015 | Stutman |
| 2015/0357069 A1 | 12/2015 | Yun et al. |
| 2016/0061963 A1* | 3/2016 | Kameshima .......... G01T 1/20 250/361 R |
| 2016/0066870 A1 | 3/2016 | Yun et al. |
| 2016/0091701 A1 | 3/2016 | Raghunathan |
| 2016/0178541 A1 | 6/2016 | Hwang et al. |
| 2016/0206259 A1 | 7/2016 | Auclair et al. |
| 2016/0336140 A1 | 11/2016 | Nonoguchi et al. |
| 2016/0341674 A1 | 11/2016 | Wu et al. |
| 2016/0351283 A1 | 12/2016 | Adler et al. |
| 2017/0038481 A1 | 2/2017 | Cheng et al. |
| 2017/0047191 A1 | 2/2017 | Yun et al. |
| 2017/0162288 A1 | 6/2017 | Yun et al. |
| 2017/0176356 A1 | 6/2017 | Hoffman et al. |
| 2017/0184520 A1 | 6/2017 | Mortensen et al. |
| 2017/0227476 A1 | 8/2017 | Zhang et al. |
| 2017/0234811 A1 | 8/2017 | Zhang et al. |
| 2017/0261442 A1 | 9/2017 | Yun et al. |
| 2017/0336334 A1 | 11/2017 | Yun et al. |
| 2018/0182131 A1 | 6/2018 | Koehler et al. |
| 2018/0202951 A1 | 7/2018 | Yun et al. |
| 2018/0261352 A1 | 9/2018 | Matsuyama et al. |
| 2018/0306734 A1 | 10/2018 | Morimoto et al. |
| 2018/0323032 A1 | 11/2018 | Strelec et al. |
| 2018/0348151 A1 | 12/2018 | Kasper et al. |
| 2019/0011379 A1 | 1/2019 | Yun et al. |
| 2019/0014243 A1* | 1/2019 | Malone ................. G02B 13/02 |
| 2019/0017946 A1 | 1/2019 | Wack et al. |
| 2019/0027265 A1 | 1/2019 | Dey et al. |
| 2019/0064084 A1 | 2/2019 | Ullom et al. |
| 2019/0086342 A1 | 3/2019 | Pois et al. |
| 2019/0115184 A1 | 4/2019 | Zalubovsky |
| 2019/0145917 A1 | 5/2019 | Yun et al. |
| 2019/0172681 A1 | 6/2019 | Owen et al. |
| 2019/0204757 A1 | 7/2019 | Brussard et al. |
| 2019/0206652 A1 | 7/2019 | Akinwande et al. |
| 2019/0212281 A1 | 7/2019 | Shchgegrov |
| 2019/0216416 A1 | 7/2019 | Koehler et al. |
| 2019/0219713 A1 | 7/2019 | Booker et al. |
| 2019/0257774 A1 | 8/2019 | Seidler et al. |
| 2019/0261935 A1 | 8/2019 | Kitamura |
| 2019/0302042 A1 | 10/2019 | Yun et al. |
| 2019/0317027 A1 | 10/2019 | Tsuboi et al. |
| 2019/0331616 A1 | 10/2019 | Schaff et al. |
| 2019/0369271 A1 | 12/2019 | Yun et al. |
| 2019/0369272 A1 | 12/2019 | Yun et al. |
| 2019/0391087 A1 | 12/2019 | Matejka et al. |
| 2020/0003712 A1 | 1/2020 | Kataoka et al. |
| 2020/0041429 A1 | 2/2020 | Cho et al. |
| 2020/0072770 A1 | 3/2020 | Yun et al. |
| 2020/0088656 A1 | 3/2020 | Pois et al. |
| 2020/0090826 A1 | 3/2020 | Adler |
| 2020/0098537 A1 | 3/2020 | Yun et al. |
| 2020/0103358 A1 | 4/2020 | Wiell et al. |
| 2020/0155088 A1 | 5/2020 | Gruener et al. |
| 2020/0158662 A1 | 5/2020 | Horiba et al. |
| 2020/0182806 A1 | 6/2020 | Kappler et al. |
| 2020/0225172 A1 | 7/2020 | Sato et al. |
| 2020/0225173 A1 | 7/2020 | Sato et al. |
| 2020/0225371 A1 | 7/2020 | Greenberg et al. |
| 2020/0232937 A1 | 7/2020 | Yaroshenko et al. |
| 2020/0279351 A1 | 9/2020 | Ratner et al. |
| 2020/0284922 A1* | 9/2020 | Wieczorek ........... G01T 1/1644 |
| 2020/0292475 A1 | 9/2020 | Cao et al. |
| 2020/0300789 A1 | 9/2020 | Osakabe et al. |
| 2020/0300790 A1 | 9/2020 | Gellineau et al. |
| 2020/0303265 A1 | 9/2020 | Gellineau et al. |
| 2020/0319120 A1 | 10/2020 | Kitamura et al. |
| 2020/0337659 A1 | 10/2020 | Sano et al. |
| 2020/0378905 A1 | 12/2020 | Safai |
| 2020/0378908 A1 | 12/2020 | Fujimura et al. |
| 2021/0055237 A1 | 2/2021 | Shchegrov et al. |
| 2021/0080408 A1 | 3/2021 | Yun et al. |
| 2021/0231588 A1* | 7/2021 | Karim ................. A61B 6/5205 |
| 2021/0255123 A1 | 8/2021 | Koskinen et al. |
| 2021/0356412 A1 | 11/2021 | Yun et al. |
| 2022/0003694 A1 | 1/2022 | Seidler et al. |
| 2022/0082515 A1 | 3/2022 | Yun et al. |
| 2022/0178851 A1 | 6/2022 | Yun et al. |
| 2022/0236199 A1* | 7/2022 | Adler ................... G01N 23/044 |
| 2023/0148975 A1* | 5/2023 | Damiano .............. A61B 6/032 378/19 |

FOREIGN PATENT DOCUMENTS

| | | |
|---|---|---|
| CN | 101257851 B | 9/2008 |
| CN | 101532969 B | 9/2009 |
| CN | 101566591 A | 10/2009 |
| CN | 101576515 A | 11/2009 |

(56) References Cited

FOREIGN PATENT DOCUMENTS

| | | |
|---|---|---|
| CN | 101413905 A | 3/2011 |
| CN | 102325498 B | 1/2012 |
| CN | 102507623 A | 6/2012 |
| CN | 102551761 A | 7/2012 |
| CN | 103604818 A | 2/2014 |
| CN | 104264228 A | 1/2015 |
| CN | 104068875 A | 5/2017 |
| CN | 206531787 U | 9/2017 |
| EP | 0751533 | 1/1997 |
| EP | 1169713 | 1/2006 |
| EP | 3168856 A2 | 5/2017 |
| JP | H04-285847 A | 10/1992 |
| JP | H06-188092 | 7/1994 |
| JP | H07-194592 | 8/1995 |
| JP | H08-128971 | 5/1996 |
| JP | H08-184572 | 7/1996 |
| JP | H09-166488 | 6/1997 |
| JP | H11-304728 | 11/1999 |
| JP | H11-352079 | 12/1999 |
| JP | 2001-021507 | 1/2001 |
| JP | 2001-124711 | 5/2001 |
| JP | 2001-235437 | 8/2001 |
| JP | 2002-214165 | 7/2002 |
| JP | 2003-149392 | 5/2003 |
| JP | 2006-501444 | 1/2006 |
| JP | 2007-212272 A | 8/2007 |
| JP | 2007-218683 | 8/2007 |
| JP | 2008-200359 | 4/2008 |
| JP | 2008-145111 | 6/2008 |
| JP | 2008-197495 | 8/2008 |
| JP | 2009-195349 | 3/2009 |
| JP | 2010-032341 A | 2/2010 |
| JP | 2010-236986 | 10/2010 |
| JP | 2011-033537 | 2/2011 |
| JP | 2011-095224 | 5/2011 |
| JP | 2011-218147 | 11/2011 |
| JP | 2012-032387 | 2/2012 |
| JP | 2012-187341 | 10/2012 |
| JP | H06-102399 A | 10/2012 |
| JP | 2012-254294 | 12/2012 |
| JP | 2013-508683 | 3/2013 |
| JP | 2013-096750 | 5/2013 |
| JP | 2013-113782 | 6/2013 |
| JP | 2013-529984 | 7/2013 |
| JP | 2013-181811 | 9/2013 |
| JP | 2014-178130 | 9/2014 |
| JP | 2015-047306 | 3/2015 |
| JP | 2015-072263 | 4/2015 |
| JP | 2015-077289 | 4/2015 |
| JP | 2017-040618 | 2/2017 |
| KR | 10-2004-0072780 | 8/2004 |
| KR | 10-2006-0088272 A | 8/2006 |
| KR | 10-2012-0012391 | 2/2012 |
| KR | 10-2012-0091591 A | 8/2012 |
| KR | 10-2014-0059688 | 5/2014 |
| WO | WO 1998/041992 | 9/1998 |
| WO | WO 2007/125833 | 11/2007 |
| WO | WO 2008/068044 | 6/2008 |
| WO | WO 2009/104560 | 8/2009 |
| WO | WO 2011/032572 | 3/2011 |
| WO | WO 2012/032950 | 3/2012 |
| WO | WO 2013/004574 | 1/2013 |
| WO | WO 2013/111050 | 8/2013 |
| WO | WO 2013/160153 | 10/2013 |
| WO | WO 2015/066333 | 5/2015 |
| WO | WO 2015/168473 | 11/2015 |
| WO | WO 2015/176023 | 11/2015 |
| WO | WO 2015/187219 | 12/2015 |
| WO | WO 2016/187623 | 11/2016 |
| WO | WO 2017/031740 | 3/2017 |
| WO | WO 2017/213996 | 12/2017 |
| WO | WO 2018/122213 | 7/2018 |
| WO | WO 2018/175570 | 9/2018 |

OTHER PUBLICATIONS

Altapova et al., "Phase contrast laminography based on Talbot interferometry," Opt. Express, vol. 20, No. 6, (2012) pp. 6496-6508.
Anklamm et al., "A novel von Hamos spectrometer for efficient X-ray emission spectroscopy in the laboratory," Rev. Sci. Instr. vol. 85 p. 053110 (2014).
Bachucki et al., "Laboratory-based double X-ray spectrometer for simultaneous X-ray emission and X-ray absorption studies," J. Anal. Atomic Spectr. DOI:10.1039/C9JA00159J (2019).
Baron et al., "A compact optical design for Bragg reflections near backscattering," J. Synchrotron Rad., vol. 8 (2001), pp. 1127-1130.
Bauer et al., "Increasing the sensitivity of micro X-ray fluorescence spectroscopy through an optimized adaptation of polycapillary lenses to a liquid metal jet source," J. Anal. At. Spectrum. DOI:10.1039/d1ja00295c (2021).
Bech, "X-ray imaging with a grating interferometer," University of Copenhagen PhD. Thesis, (May 1, 2009).
Bech, "In-vivo dark-field and phase-contrast x-ray imaging," Scientific Reports 3, (2013), Article No. 03209.
Bertaux et al., "Sub-pixel high-resolution imaging of high-energy x-rays inspired by sub-wavelength optical imaging," Op. Express, vol. 29, No. 22-25, p. 35003 (2021).
Birkholz, "Chapter 4: Grazing Incidence Configurations," Thin Film Analysis by X-ray Scattering (Wiley-VCH Verlag Gmbh & Co. KGaA, Weinheim, Germany, 2006).
Birnbacher et al., "Quantitative X-ray phase contrast computed tomography with grating interferometry," European J. of Nucl. Med. and Mol. Imaging, https://doi.org/10.1007/s00259-021-05259-6 (2021).
Bogdanowicz et al., "Model-free measurement of lateral recess in gate-all-around transistors with micro hard-X-ray fluorescence," J. Micro/Nanopattern, Mater. Metrol., vol. 22(3), pp. 034001-1-8 (2023).
Brombal et al., "PEPI Lab: a flexible compact multi-modal setup for X-ray phase-contrast and spectral imaging," Sci. Rep. 13, p. 4206, https://doi.org/10.1038/s41598-023-30316-5 (2023).
Buchanan et al., "Effective modelling of high-energy laboratory-based x-ray phase contrast imaging utilising absorption masks or gratings," J. Appl. Physics (accepted) (2020).
Chen et al., "Advance in detection of low sulfur content by wavelength dispersive XRF," Proceedings of the Annual ISA Analysis Division Symposium (2002).
Coan et al., "In vivo x-ray phase contrast analyzer-based imaging for longitudinal osteoarthritis studies in guinea pigs," Phys. Med. Biol. vol. 55(24) (2010), pp. 7649-7662.
Cohen et al., "Tunable laboratory extended x-ray absorption fine structure system," Rev. Sci. Instr. vol. 51, No. 3, Mar. 1980, pp. 273-277.
David et al., "Hard X-ray phase imaging and tomography using a grating interferometer," Spectrochimica Acta Part B vol. 62 (2007) pp. 626-630.
Davis et al., "Bridging the Micro-to-Macro Gap: A New Application for Micro X-Ray Fluorescence," Microsc Microanal., vol. 17(3) (Jun. 2011), pp. 410-417.
Detlefs et al., "Fast Chemical Contrast by X-ray Fluorescence Intensity Ratio Detection," Anal. Chem., https://doi.org/10.1021/acs.analchem.3c00623 (2023).
Dewulf et al., "Advances in the metrological traceability and performance of X-ray computed tomography," CIRP Annals—Manuf. Tech. vol. 00, 1-24 (2022).
Diaz et al., "Monte Carlo Simulation of Scatter Field for Calculation of Contrast of Discs in Synthetic CDMAM Images," In: Digital Mammography, Proceedings 10th International Workshop IWDM 2010 (Springer Verlag, Berlin Heidelberg), (2010), pp. 628-635 (9 pages).
Dibernardo, "Non-disruptive techniques for depth profiling in photoemission spectroscopy," Nature Review Physics, https://doi.org/10.1038/s42254-021-00331-4 (2021).
Dittler et al., "A mail-in and user facility for X-ray absorption near-edge structure: the CEI-XANES laboratory X-ray spectrometer at University of Washington," J. Synch. Rad. vol. 26, eight pages, (2019).

(56) References Cited

OTHER PUBLICATIONS

Dong et al., "Improving Molecular Sensitivity in X-Ray Fluorescence Molecular Imaging (XFMI) of Iodine Distribution in Mouse-Sized Phantoms via Excitation Spectrum Optimization," IEEE Access, vol. 6, pp. 56966-56976 (2018).

Du et al., "Removal of artifacts caused by grating imperfections in X-ray phase contrast tomography," J. of Inst. vol. 16, P06039, doi.org/10.1088/1748-0221/16/06/P06039 (2021).

Erko et al., "X-ray Optics," Ch. 3 of "Handbook of Practical X-Ray Fluorescence Analysis," B. Beckhoff et al., eds. (Springer, Berlin, Germany, 2006), pp. 85-198.

Espes et al., "High-resolution X-ray source with advanced e-beam technology: pushing the resolution limitation for lab-scale NanoCT," Micros. Microanal., vol. 27 (Suppl. 1), pp. 1230 (2021).

Feng et al., "Reduction of Compton Background Noise for X-ray Fluorescence Computed Tomography with Deep Learning," Photonics, vol. 9, p. 108 (2022).

Fernández-Ruiz, "TXRF Spectrometry as a Powerful Tool for the Study of Metallic Traces in Biological Systems," Development in Analytical Chemistry, vol. 1 (2014), pp. 1-14.

Fisher et al., "Laminography in the lab: imaging planar objects using a conventional x-ray CT scanner," Meas. Sci. Technol., vol. 30, p. 035401 (2019).

Flenner et al., "Hard X-ray full-field nanoimaging using a direct photon-counting detector," J. Synch. Rad., https://doi.org/10.1107/S1600577522012103 (2022).

Gaur et al., "On the method of calibration of the energy dispersive EXAFS beamline and Indus-2 and fitting theoretical model to the EXAFS spectrum," Sadhana, vol. 36, No. 3 pp. 3390348 (2011).

Ge et al., "Investigation of the partially coherent effects in a 2D Talbot interferometer," Anal. Bioanal. Chem. vol. 401, (2011), pp. 865-870.

Ge et al., "Self-absorption correction on 2D X-ray fluorescence maps," Sci. Rep. 13, p. 7271, https://doi.org/10.1038/s41598-023-33383-w (2023).

Ghani et al., "A Phase Sensitive X-ray Brest Tomosynthesis System: Preliminary Patient Images with Cancer Legions," Phys. Med. Biol. https://doi.org/10.1088/1361-6560/ac2ea6 (2021).

Graetz et al., "Lenseless C-ray Nano-Tomography down to 150 nm Resolution: On the Quantification of Modulation Transfer and Focal Spot of the Lab-based ntCT System," arXiv:2009.11749v1 [physics.ins-det] Sep. 24, 2020, 10 pages.

Günther et al., "Full-field structured-illumination super-resolution X-ray transmission microscopy," Nature Comm. 10:2494 (2019) and supplementary information.

Gustschin et al., "High resolution and sensitivity bi-directional x-ray phase contrast imaging using 2D Talbot array illuminators," arXiv:2105.07347v1 [physics.med-ph] May 16, 2021.

Harasse et al., "X-ray Phase Laminography with Talbot Interferometer", in Developments in X-Ray Tomography VII, Proc. SPIE vol. 7804 (2010), 780411.

Harasse et al., "Iterative reconstruction in x-ray computed laminography from differential phase measurements", Opt. Express. vol. 19 (2011), pp. 16560-16573.

Harasse et al., "X-ray Phase Laminography with a Grating Interferometer using Iterative Reconstruction", in International Workshop on X-ray and Neutron Phase Imaging with Gratings, AIP Conf. Proc. vol. 1466, (2012), pp. 163-168.

Hashimoto et al., "Improved reconstruction method for phase stepping data with stepping errors and dose fluctuations," Optics Express, vol. 28, No. 11, pp. 16363-16384 (2020).

Haug et al., A laboratory-based multifunctional near ambient pressure X-ray photoelectron spectroscopy system for electrochemical, catalytic, and cryogenic studies, Rev. Sci. Instr. vol. 94, 065104, https://doi.org/10.1063/5.0151755 (2023).

Heirwegh et al., "The focused beam X-ray fluorescence elemental quantification software package PIQUANT," Spectrochimica Acta Part B: Atomic Spectroscopy, https://doi.org/10/1016/j.sab.2022.106520 (2022).

Hemraj-Benny et al., "Near-Edge X-ray Absorption Fine Structure Spectroscopy as a Tool for Investigating Nanomaterials," Small, vol. 2(1), (2006), pp. 26-35.

Hennekam et al., "Trace metal analysis of sediment cores using a novel X-ray fluorescence core scanning method," Quaternary Int'l, https://doi.org/10.1016/j.quaint.2018.10.018 (2018).

Hirano et al., "X-ray zooming optics for analyzer-based multi-contrast computed tomography," J. Synch. Rad. vol. 29, https://doi.org/10.1107/S1600577522001412 (2022).

Holberg et al., "High-Resolution Table-Top NEXAFS Spectroscopy," Anal. Chem. https://10.1021/acs.analchem.1c04374 (2022).

Holfelder et al., "A double crystal von Hamos spectrometer for traceable x-ray emission spectroscopy," Rev. Sci. Instrum. vol. 92, p. 123105 (2021).

Honma et al., Full-automatic XAFS Measurement System of the Engineering Science Research II beamline BL14B2 at Spring-8, 2011, AIP Conference Proceedings 1234, pp. 13-16.

Hoshino et al., "High-energy X-ray micro-laminography to visualize microstructures in dense planar object," J. Synch. Rad. https://doi.org/10.1107/S1600577522012176, 2023 publication year.

Howard et al., "High-Definition X-ray Fluorescence Elemental Mapping of Paintings," Anal. Chem., 2012, vol. 84(7), pp. 3278-3286.

Hu et al., "Improving small animal cone beam CT resolution by mitigating x-ray focal spot induced blurring via deconvolution," Phys. Med. Bio., in press, https://doi.org/10.1088/1361-6560/ac6b7a (2022).

Ide-Ektessabi et al., "The role of trace metallic elements in neurodegenerative disorders: quantitative analysis using XRF and XANES spectroscopy," Anal. Sci., vol. 21(7) (Jul. 2005), pp. 885-892.

Ishisaka et al., "A New Method of Analyzing Edge Effect in Phase Contrast Imaging with Incoherent X-rays," Optical Review, vol. 7, No. 6, (2000), pp. 566-572.

Ito et al., "A Stable In-Laboratory EXAFS Measurement System," Jap. J. Appl. Phys., vol. 22, No. 2, Feb. 1, 1983, pp. 357-360.

Itoh et al., "Two-dimensional grating-based X-ray phase-contrast imaging using Fourier transform phase retrieval," Op. Express, vol. 19, No. 4 (2011) pp. 3339-3346.

Janssens et al., "Recent trends in quantitative aspects of microscopic X-ray fluorescence analysis," TrAC Trends in Analytical Chemistry 29.6 (Jun. 2010): 464-478.

Jahrman et al., "Vacuum formed temporary spherically and toroidally bent crystal analyzers for x-ray absorption and x-ray emission spectroscopy," Rev. Sci. Inst. vol. 90, 013106 (2019).

Jiang et al., "X-Ray Phase-Contrast Imaging with Three 2D Gratings," Int. J. Biomed. Imaging, (2008), 827152, 8 pages.

Kalasová et al., "Characterization of a laboratory-based X-ray computed nanotomography system for propagation-based method of phase contrast imaging," IEEE Trans. On Instr. And Meas., DOI 10.1109/TIM.2019.2910338 (2019).

Keyrilainen et al., "Phase contrast X-ray imaging of breast," Acta Radiologica, vol. 51 (8), (2010), pp. 866-884.

Khan et al., "Recent Trends in Applications of X-ray Photoelectron Spectroscopy (XPS) Technique in Coatings for Corrosion Protection," Chapter of "Recent Developments in Analytical Techniques for Corrosion Research," I. Toor (ed.), Springer Nature Switzerland AG https://doi.org/10.1007/978-3-030-89101-5_8 (2022).

Kido et al., "Bone Cartilage Imaging with X-ray Interferometry using a Practical X-ray Tube", in Medical Imaging 2010: Physics of Medical Imaging, Proc. SPIE vol. 7622 (2010), 762240.

Kim, "Talbot images of wavelength-scale amplitude gratings," Opt. Express vol. 20(5), (2012), pp. 4904-4920.

Kim et al., "Observation of the Talbot Effect at Beamline 6C Bio Medical Imaging of the Pohang Light Source—II," J. Korean Phys. Soc., vol. 74, No. 10, pp. 935-940 (May 2019).

Kim et al., "A Simulation Study on the Transfer Characteristics of the Talbot Pattern Through Scintillation Screens in the Grating Interferometer," J. Rad. Sci. and Tech. 42(1), pp. 67-75 (2019).

Kiranjot et al., "Surface and interface characterization of Ru/C/Ru trilayer structure using grazing incidence X-ray reflectivity and X-ray fluorescence," Surf. And Interface Analysis, doi: 10.1002/sia7016 (2021).

(56) References Cited

OTHER PUBLICATIONS

Kiyohara et al., "Development of the Talbot-Lau Interferometry System Available for Clinical Use", in International Workshop on X-ray and Neutron Phase Imaging with Gratings, AIP Cong. Proc. vol. 1466, (2012), pp. 97-102.
Klockenkämper et al., "7.1 Instrumental Developments" and "7.3 Future Prospects by Combinations," from Chapter 7 of Total Reflection X-ray Fluorescence Analysis and Related Methods 2nd Ed. (J. Wiley and Sons, Hoboken, NJ, 2015).
Klockenkämper et al., "Chapter 3: Instrumentation for TXRF and GI-XRF," Total Reflection X-ray Fluorescence Analysis and Related Methods 2nd Ed. (J. Wiley and Sons, Hoboken, NJ, 2015).
Kottler et al., "A two-directional approach for grating based differential phase contrast imaging using hard x-rays," Opt. Express vol. 15(3), (2007), pp. 1175-1181.
Kottler et al., "Dual energy phase contrast x-ray imaging with Talbot-Lau interferometer," J. Appl. Phys. vol. 108(11), (2010), 114906.
Kulow et al., "On the Way to Full-Field X-ray Fluorescence Spectroscopy Imaging with Coded Apertures," J. Anal. At. Spectrom. Doi: 10.1039/C9JA00232D (2019).
Kuwabara et al., "Hard-X-ray Phase-Difference Microscopy with a Low-Brilliance Laboratory X-ray Source", Appl. Phys. Express vol. 4 (2011) 062502.
Leatham et al., "X-ray dark-field and phase retrieval without optics, via the Fokker-Planck equation," arXiv:2122.10999v1, physics.med-ph, Dec. 21, 2021.
Lei et al., "8-inch-diameter field of view for X-ray differential phase-contrast imaging," Nucl. Inst. And Methods in Physics Research A, https://doi.org/10-1016/j.nima.2021.165375 (2021).
Li et al., "X-ray phase-contrast imaging using cascade Talbot-Lau interferometers," Proc. SPIE 10964 (2018), pp. 1096469-1-1096469-6.
Lin et al., "Quasi-Monte Carlo method for calculating X-ray scatter in CT," Op. Express, vol. 29, No. 9, p. 13746 (2021).
Lohmann et al., "An interferometer based on the Talbot effect," Optics Communications vol. 2 (1971), pp. 413-415.
Longo et al., "Flexible Plenoptic X-ray Microscopy," Photonics, vol. 9, p. 98 (2022).
Lübcke et al., "Soft X-ray nanoscale imaging using a sub-pixel resolution charge coupled device (CCD) camera," Rev. Sci. Instrum. vol. 90, 043111 (2019).
Lühl et al., "Scanning transmission X-ray microscopy with efficient X-ray fluorescence detection (STXM-XRF) for biomedical applications in the soft and tender energy range," J. Synch. Rad. vol. 26, https://doi.org/10.1107/S1600577518016879, (2019).
Malzer et al., "A laboratory spectrometer for high throughput X-ray emission spectroscopy in catalysis research," Rev. Sci. Inst. 89, 113111 (2018).
Mamyrbayev et al., "Staircase array of inclined refractive multi-lenses for large field of view pixel super-resolution scanning transmission hard X-ray microscopy," J. Synch. Rad., vol. 28 https://doi.org/10.1107/S1600577521001521 (2021).
Matsunaga et al., "Development of projection X-ray microscope with 10 nm spot size," Nodestr. Test. And Eval., https://doi.org.10.1080/10589759.2022.2083616 (2022).
Matsuyama et al., "Wavefront measurement for a hard-X-ray nanobeam using single-grating interferometry", Opt Express vol. 20 (2012), pp. 24977-24986.
Menzies et al., "Dual source X-ray and electron SEM system: Elemental mapping of an Epithermal gold-bearing sample from Karangahake, New Zealand," Microsc. Microanal., vol. 27 (Suppl. 1), pp. 456 (2021).
Miao et al., "Motionless phase stepping in X-ray phase contrast imaging with a compact source," Proceedings of the National Academy of Sciences, vol. 110(48), (2013), pp. 19268-19272.
Mijovilovich et al., "Analysis of trace metal distribution in plants with lab-based microscopic X-ray fluorescence imaging," Plant Methods, vol. 16, No. 82, 21 pages (2020).
Mizutani et al., X-ray microscopy for neural circuit reconstruction in 9th International Conference on X-Ray Microscopy, J. Phys: Conf. Ser. 186 (2009) 012092.
Modregger et al., "Grating-Based X-ray Phase Contrast Imaging," Ch. 3 of Emerging Imaging Technologies in Medicine, M. Anastasio & P. La Riviere, ed., CRC Press, Boca Raton, FL, (2012), pp. 43-56.
Momose et al., "Phase-Contrast X-Ray Imaging Using an X-Ray Interferometer for Biological Imaging", Analytical Sciences vol. 17 Supplement (2001), pp. i527-i530.
Momose et al., "Demonstration of X-Ray Talbot Interferometry", Jpn. J. Appl. Phys. vol. 42 (2003), pp. L866-L868.
Momose et al., "Phase Tomography Using an X-ray Talbot Interferometer", in Developments in X-Ray Tomography IV, Proc. SPIE vol. 5535 (2004), pp. 352-360.
Momose, "Recent Advances in X-ray Phase Imaging", Jpn. J. Appl. Phys. vol. 44 (2005), pp. 6355-6367.
Momose et al., "Biomedical Imaging by Talbot-Type X-Ray Phase Tomography" in Developments in X-Ray Tomography V, Proc. SPIE vol. 6318 (2006) 63180T.
Momose et al., "Phase Tomography by X-ray Talbot Interferometry for Biological Imaging" Jpn. J. Appl. Phys. vol. 45 2006 pp. 5254-5262.
Momose et al., "X-ray Talbot Interferometry with Capillary Plates", Jpn. J. Appl. Phys. vol. 45 (2006), pp. 314-316.
Momose et al., "Phase Imaging with an X-ray Talbot Interferometer", Advances in X-ray Analysis vol. 49(3) (2006), pp. 21-30.
Momose et al., "Phase Tomography Using X-ray Talbot Interferometer", in Synchrotron Radiation Instrumentation: Ninth International Conference, AIP Conf. Proc. vol. 879 (2007), pp. 1365-1368.
Momose et al., "Sensitivity of X-ray Phase Imaging Based on Talbot Interferometry", Jpn. J. Appl. Phys. vol. 47 (2008), pp. 8077-8080.
Momose et al., "Grating-Based X-ray Phase Imaging Using Multiline X-ray Source", Jpn. J. Appl. Phys. vol. 48 (2009), 076512.
Momose et al., "X-ray phase tomography with a Talbot interferometer in combination with an X-ray imaging microscope", in 9th International Conference on X-Ray Microscopy, J. Phys: Conf. Ser. 186 (2009) 012044.
Momose et al., "High-speed X-ray phase imaging and X-ray phase tomography with Talbot interferometer and white synchrotron radiation", Opt. Express vol. 17 (2009), pp. 12540-12545.
Momose et al., "X-Ray Phase Imaging with Talbot Interferometry", in "Biomedical Mathematics: Promising Directions in Imaging, Therapy Planning, and Inverse Problems", Y. Censor, M. Jiang & G.Wang, eds. (Medical Physics Publishing, Madison, WI, USA, 2010), pp. 281-320.
Momose et al., "X-ray Phase Measurements with Talbot Interferometry and Its Applications", in International Conference on Advanced Phase Measurement Methods in Optics and Imaging, AIP Conf. Proc. vol. 1236 (2010), pp. 195-199.
Momose et al., "X-ray Phase Imaging Using Lau Effect", Appl. Phys. Express vol. 4 (2011) 066603.
Momose et al., "Four-dimensional X-ray phase tomography with Talbot interferometry and white synchrotron radiation: dynamic observation of a living worm", Opt. Express vol. 19 (2011), pp. 8423-8432.
Momose et al., "X-ray Phase Imaging—From Static Observation to Dynamic Observation—", in International Workshop on X-ray and Neutron Phase Imaging with Gratings AIP Conf. Proc. vol. 1466, (2012), pp. 67-77.
Momose et al., "Recent Progress in X-ray and Neutron Phase Imaging with Gratings," Quantum Beam Science, vol. 4, No. 9; doi:10.3390/qubs4010009 (2020).
Morimoto et al., "X-ray phase contrast imaging by compact Talbot-Lau interferometer with a signal transmission grating," 2014, Optics Letters, vol. 39, No. 15, pp. 4297-4300.
Morimoto et al., "Design and demonstration of phase gratings for 2D single grating interferometer," Optics Express vol. 23, No. 23, 29399 (2015).
Munro et al., Design of a novel phase contrast imaging system for mammography, 2010, Physics in Medicine and Biology, vol. 55, No. 14, pp. 4169-4185.

(56) References Cited

OTHER PUBLICATIONS

Nango et al., "Talbot-defocus multiscan tomography using the synchrotron X-ray microscope to study the lacuno-canalicular network in mouse bone", Biomed. Opt. Express vol. 4 (2013), pp. 917-923.
Nemeth et al., "Laboratory von Hamos X-ray Spectroscopy for Routine Sample Characterization," arvix:1607.08045v1 (2016).
Neuhausler et al., "Non-destructive high-resolution X-ray imaging of ULSI micro-electronics using keV X-ray microscopy in Zernike phase contrast," Microelectronic Engineering, Elsevier Publishers BV., Amsterdam, NO vol. 83, No. 4-9 (Apr. 1, 2006) pp. 1043-1046.
Newville, "Fundamentals of XAFS," (Univ. of Chicago, Chicago, IL, Jul. 23, 2004).
Nykanen et al., "X-ray scattering in full-field digital mammography," Med. Phys. vol. 30(7), (2003), pp. 1864-1873.
O'Brien et al., "Recent Advances in X-ray Cone-beam Computed Laminography," J. X-ray Sci. and Tech., vol. 24, No. 5, pp. 691-707 (2016).
Ohba et al., "Laboratory-size x-ray microscope using Wolter mirror optics and an electron-impact x-ray source," Rev. Sci. Inst. 92, 093704 (2021).
Oji et al., Automatic XAFS measurement system developed at BL14B2 in SPring-8, Available online Nov. 15, 2011, Journal of Synchrotron Radiation, vol. 19, pp. 54-59.
Okolo, "A guide into the world of high-resolution 3D imaging: the case of soft X-ray tomography for the life sciences," Biochem. Soc. Trans., https://doi.org/10.1042/BST20210886 (2002).
Olbinado et al., "Demonstration of Stroboscopic X-ray Talbot Interferometry Using Polychromatic Synchrotron and Laboratory X-ray Sources", Appl. Phys. Express vol. 6 (2013), 096601.
Ortega et al., "Bio-metals imaging and speciation in cells using proton and synchrotron radiation X-ray microspectroscopy," J. Royal Society Interface vol. 6 suppl. 5 (Oct. 6, 2009), pp. 6S649-58.
Pandeshwar et al., "Envelope modulated x-ray grating interferometry," Appl. Phys. Lett. 120, 193701 (2022).
Pandeshwar et al., "Modeling of beam hardening effects in a dual-phase X-ray grading interferometer for quantitative dark-field imaging," Optics Express, vol. 28, No. 13, Jun. 22, 2020, pp. 19187-19204 (2020).
Parrill et al., "GISAXS—Glancing Incidence Small Angle X-ray Scattering," Journal de Physique IV, vol. 3 (Dec. 1993), pp. 411-417.
Paunesku et al., "X-Ray Fluorescence Microprobe Imaging in Biology and Medicine," J. Cell. Biochem. vol. 99, pp. 1489-1502 (2006).
Pekel et al., "Geometric calibration of seven degree of freedom robotic sample holder for x-ray CT," Proc. Of SPIE 12304, 7th Int'l Conf. on Image Formation in X-Ray Computed Tomography, 123042L, doi:10.1117/12.2646492 (2022).
Pfeiffer et al., "Phase retrieval and differential phase-contrast imaging with low-brilliance X-ray sources," Nature Physics vol. 2, (2006), pp. 258-261.
Pfeiffer et al., "Hard x-ray phase tomography with low brilliance x-ray sources," Phys. Rev. Lett. vol. 98, (2007), 108105.
Pfeiffer et al., "Hard-X-ray dark-field imaging using a grating interferometer," Nature Materials vol. 7, (2008), pp. 134-137.
Pfeiffer, "Milestones and basic principles of grating-based x-ray and neutron phase-contrast imaging," in International Workshop on X-ray and Neutron Phase Imaging with Gratings AIP Conf. Proc. vol. 1466, (2012), pp. 2-11.
Pianetta et al., "Application of synchrotron radiation to TXRF analysis of metal contamination on silicon wafer surfaces," Thin Solid Films, vol. 373(1-2), 2000, pp. 222-226.
Potts, "Electron Probe Microanalysis", Ch. 10 of "A Handbook of Silicate Rock Analysis" (Springer Science + Business Media, New York, 1987), pp. 326-382.
Prewitt et al., "Focused ion beam repair: staining of photomasks and reticles," J. Phys. D Appl. Phys. vol. 26 (1993), pp. 1135-1137.
Prewitt et al., "Gallium Staining in FIB Repair of Photomasks," Microelectronic Engineering, vol. 21 (1993), pp. 191-196.
Prewitt et al., "FIB Repair of 5X Reticles and Effects on IC Quality," Integrated Circuit Metrology, Inspection, and Process Control VII, Proc. SPIE vol. 1926 (1993), pp. 517-526.
Pushie et al., "Prion protein expression level alters regional copper, iron and zinc content in the mouse brain," Metallomics vol. 3, 206-214 (2011).
Pushie et al., "Elemental and Chemically Specific X-ray Fluorescence Imaging of Biological Systems," Chem. Rev. 114:17, 8499-8541 (2014).
Qiao et al., "Single-shot x-ray phase-contrast and dark-field imaging based on coded binary phase mask," Appl. Phys. Lett. 119, 011105 (2021).
Qin et al., "Trace metal imaging with high spatial resolution: Applications in biomedicine," Metallomics, vol. 3 (Jan. 2011), pp. 28-37.
Redus et al., "Spectrometer configuration and measurement uncertainty in X-ray spectroscopy," X-Ray Spectrom., pp. 1-14 (2020).
Renaud et al., "Probing surface and interface morphology with Grazing Incidence Small Angle X-ray Scattering," Surface Science Reports, vol. 64:8 (2009), pp. 255-380.
Rix et al., "Super-Resolution X-ray phase-contrast and dark-field imaging with a single 2D grating and electromagnetic source stepping," Phys. Med. Biol. In press https://doi.org/10.1088/1361-6560/ab2ff5 (2019).
Rutishauser, "X-ray grating interferometry for imaging and metrology," 2003, Eth Zurich, Diss. ETH No. 20939.
Sato et al., Two-dimensional gratings-based phase-contrast imaging using a conventional x-ray tube, 2011, Optics Letters, vol. 36, No. 18, pp. 3551-3553.
Scherer et al., "Bi-Directional X-Ray Phase-Contrast Mammography," PLoS One, vol. 9, Issue 5 (May 2014) e93502.
Scholze et al., "X-ray Detectors and XRF Detection Channels," Ch. 4 of "Handbook of Practical X-Ray Fluorescence Analysis," B. Beckhoff et al., eds. (Springer, Berlin Heidelberg, Germany, 2006), pp. 85-198.
Schunck et al., "Soft x-ray imaging spectroscopy with micrometer resolution," Optica vol. 8, No. 2, pp. 156-160 (2021).
Seddon-Ferretti et al., "HERMES—a GUI-based software tool for pre-processing of X-ray absorption spectroscopy data from laboratory Rowland circle spectrometers," J. Synch. Rad., vol. 29, https://doi.org/10.1107/S1600577521012583, pp. 1-4 (2022).
Seifert et al., "Talbot-Lau x-ray phase-contrast setup for fast scanning of large samples," Sci. Rep. 9:4199, pp. 1-11 (2019).
Shi et al., "Laboratory X-ray interferometry imaging with a fan-shaped source grating," Optics Lett., doi.org/10.1364/OL.426867 (2021).
Shimura et al., "Hard x-ray phase contrast imaging using a tabletop Talbot-Lau interferometer with multiline embedded x-ray targets", Opt. Lett. vol. 38(2) (2013), pp. 157-159.
Simionovici et al., "X-ray focusing methods for X-ray absorption spectroscopy," Int'l Tables Crystallog. vol. I, https://doi.org/10.1107/S1574870721006844 (2022).
Soltau et al., "Coherent Diffractive Imaging with Diffractive Optics," Phys. Rev. Lett. 128, 223901 (2022).
Sparks Jr., "X-ray Fluorescence Microprobe for Chemical Analysis," in Synchrotron Radiation Research, H. Winick & S. Doniach, eds. (Plenum Press, New York, NY 1980), pp. 459-512.
Stampanoni et al., "The First Analysis and Clinical Evaluation of Native Breast Tissue Using Differential Phase-Contrast Mammography," Investigative Radiology, vol. 46, pp. 801-806. pub Dec. xx, 2011.
Storm et al., "Optimizing the energy bandwidth for transmission full-field X-ray microscopy experiments," J. Synch. Rad., vol. 29, https://doi.org/10.1107/S1600577521011206, pp. 1-10 (2022).
Streli et al., "Micro-X-ray fluorescence spectroscopy," Chapter I.9.f of "Imaging Modalities for Biological and Preclinical Research: A compendium, vol. 1, Part I: Ex vivo biological imaging," Ed. Walter et al., 8 pages, doi:10.1088/978-0-7503-3059-6ch42 (2021).
Sunday et al., "X-ray Metrology for the Semiconductor Industry Tutorial," J. Res. Nat'l Inst. Stan. vol. 124: 124003 (2019); https://doi.org/10.6028/jres.124.003.
Takeda et al., "X-Ray Phase Imaging with Single Phase Grating", Jpn. J. Appl. Phys. vol. 46 (2007), pp. L89-L91.

(56) References Cited

OTHER PUBLICATIONS

Takeda et al., "Differential Phase X-ray Imaging Microscopy with X-ray Talbot Interferometer" Appl. Phys. Express vol. 1 (2008) 117002.
Talbot, "Facts relating to optical science No. IV," Philos. Mag. vol. 9 (1836), pp. 401-407.
Tanaka et al., "Cadaveric and in vivo human joint imaging based on differential phase contrast by X-ray Talbot-Lau interferometry", Z. Med. Phys. vol. 23 (2013), pp. 222-227.
Tanaka et al., "Propagation-based phase-contrast imaging method for full-field X-ray microscopy using advanced Kirkpatrick-Baez mirrors," Op. Express vol. 31, No. 16, pp. 26135-26144 (2023).
Tang et al., "Detailed analysis of the interference patterns measured in lab-based X-ray dual-phase grating interferometry through wave propagation simulation," Opt. Ex. vol. 31, No. 2, pp. 1677-1691 (2023).
Tao et al., "Moire artifacts reduction in Talbot-Lau X-ray phase contrast imaging using a three-step iterative approach," Opt. Ex. vol. 30, No. 20, pp. 35096-35111 (2022).
Tao et al., "Factors Affecting the Spatial Resolution in 2D Grating-Based X-Ray Phase Contrast Imaging," Frontiers in Physics, doi: 10.3389/fphy.2021.672207 (2021).
Taphorn et al., "Grating-based spectral X-ray dark-field imaging for correlation with structural size measures," Sci. Reports, vol. 10, 13195 (2020).
Tebina et al., "X-Ray Fault Injection: Reviewing Defensive Approaches from a Security Perspective," 2022 IEEE Int'l Symp. Defect and Fault Tolerances in VLSI and Nanotechnology Systems (DFT), doi: 10.1109/DFT56152.2022.9962362 (2022).
Terzano et al., Recent advances in analysis of trace elements in environmental samples by X-ray based techniques (IUPAC Technical Report), Pure Appl. Chem. 2019.
Tessarini et al., "Semi-classical Monte Carlo algorithm for the simulation of X-ray grating interferometry," Sci. Rep. vol. 12, p. 2485 (2022).
Tetef et al., "Unsupervised Machine Learning for Unbiased Chemical Classification in X-ray Absorption Spectroscopy and X-ray Emission Spectroscopy," Royal Soc. of Chem. Doi: 10.33774/chemrxiv-2021-5tvrv (2021).
Titus et al., "Advancing the in-situ characterization of light elements via X-ray absorption spectroscopy using superconducting detectors," Microsc. Microanal., vol. 27, (Suppl. 1), pp. 2890 (2021).
Tkachuk et al., "High-resolution x-ray tomography using laboratory sources", in Developments in X-Ray Tomography V, Proc. SPIE 6318 (2006): 631810.
Tkachuk et al., "Multi-length scale x-ray tomography using laboratory and synchrotron sources", Microsc. Microanal. vol. 13 (Suppl. 2) (2007), pp. 1570-1571.
Töpperwien et al., "Multiscale x-ray phase-contrast tomography in a mouse model of transient focal cerebral ischemia," Biomed. Op. Express, vol. 10, No. 1, Jan. 2019, pp. 92-103.
Tsuji et al., "X-Ray Spectrometry: Recent Technological Advances," John Wiley & Sons Ltd. Chichester, West Sussex, UK 2004), Chapters 1-7.
Udagawa, "An Introduction to In-House EXAFS Facilities," The Rigaku Journal, vol. 6, (1) (1989), pp. 20-27.
Udagawa, "An Introduction to X-ray Absorption Fine Structure," The Rigaku Journal, vol. 11(2)(1994), pp. 30-39.
Uehara et al., "Effectiveness of X-ray grating interferometry for non-destructive inspection of packaged devices", J. Appl. Phys. vol. 114 (2013), 134901.
Viermetz et al., "High resolution laboratory grating-based X-ray phase-contrast CT," Scientific Reports 8:15884 (2018).
Vila-Comamala et al., "High sensitivity X-ray phase contrast imaging by laboratory grating-based interferometry at high Talbot order geometry," Op. Express vol. 29, No. 2, pp. 2049-2064 (2021).
Vogt, "X-ray Fluorescence Microscopy: A Tool for Biology, Life Science and Nanomedicine," Presentation on May 16, 2012 at James Madison Univ., Harrisonburg, VA (31 slides), 2012.
Wan et al., "Fabrication of Multiple Slit Using Stacked-Sliced Method for Hard X-ray Talbot-Lau Interferometer", Jpn. J. Appl. Phys. vol. 47 (2008), pp. 7412-7414.
Wang et al., "Advantages of intermediate X-ray energies in Zernike phase contrast X-ray microscopy," Biotech. Adv., vol. 31 (2013) pp. 387-392.
Weitkamp et al., "Hard X-ray phase imaging and tomography with a grating interferometer," Proc. SPIE vol. 5535, (2004), pp. 137-142.
Weitkamp et al., "X-ray phase imaging with a grating interferometer," Opt. Express vol. 13(16), (2005), pp. 6296-6304.
Weitkamp et al., "X-ray wavefront analysis and optics characterization with a grating interferometer," Appl. Phys. Lett. vol. 86, (2005), 054101.
Weitkamp et al., Tomography with grating interferometers at low-brilliance sources, 2006, SPIE, vol. 6318, pp. 0S-1 to 0S-10.
Weitkamp et al., "X-ray wavefront diagnostics with Talbot interferometers," International Workshop on X-Ray Diagnostics and Scientific Application of the European XFEL, Ryn, Poland, (2010), 36 slides.
Weitkamp et al., "Design aspects of X-ray grating interferometry," in International Workshop on X-ray and Neutron Phase Imaging with Gratings AIP Conf. Proc. vol. 1466, (2012), pp. 84-89.
Wen et al., "Fourier X-ray Scattering Radiography Yields Bone Structural Information," Radiology, vol. 251 (2009) pp. 910-918.
Wen et al., "Single-shot x-ray differential phase-contrast and diffraction imaging using two-dimensional transmission gratings," Op. Lett. vol. 35, No. 12, (2010) pp. 1932-1934.
Wilde et al., "Modeling of an X-ray grating-based imaging interferometer using ray tracing," Op. Express vol. 28, No. 17, p. 24657 (2020).
Wilde et al., "Statistical optics modeling of dark-field scattering in X-ray grating interferometers: Part 1. Theory," Op. Express vol. 29, No. 25, p. 40891 (2021).
Wilde et al., "Statistical optics modeling of dark-field scattering in X-ray grating interferometers: Part 2. Simulation," Op. Express vol. 29, No. 25, p. 40917 (2021).
Withers et al., "X-ray computed tomography," Nature Reviews | Methods Primers, vol. 1, No. 18, pp. 1-21 (2021).
Witte et al., "From 2D STXM to 3D Imaging: Soft X-ray Laminography of Thin Specimens," Nano Lett. vol. 20, pp. 1305-1314 (2020).
Wittry et al., "Properties of fixed-position Bragg diffractors for parallel detection of x-ray spectra," Rev. Sci. Instr. vol. 64, pp. 2195-2200 (1993).
Wobrauschek et al., "Micro XRF of light elements using a polycapillary lens and an ultra-thin window Silicon Drift Detector inside a vacuum chamber," 2005, International Centre for Diffraction Data 2005, Advances in X-ray Analysis, vol. 48, pp. 229-235.
Wobrauschek et al., "Energy Dispersive, X-Ray Fluorescence Analysis," Encyclopedia of Analytical Chemistry, R.A. Meyers, Ed. (Wiley 2010).
Woicik et al., "Soft X-ray absorption spectra," Int. Tables Crystallogr. vol. 1, https://doi.org.10.1107/S1574870720008484 (2023).
Xiao et al., "TXM-Sandbox: an open-source software for transmission X-ray microscopy data analysis," J. Synch. Rad., vol. 29, https://doi.org/10.1107/S1600577521011978, p. 1-10 (2022).
Xu et al., "Synchrotron radiation computed laminography for polymer composite failure studies," J. Synch. Rad., vol. 17, pp. 222-226 (2010).
Xu et al., "Comparison of image quality in computed laminography and tomography," Op. Express, vol. 20, No. 2, pp. 794-806 (2012).
Yamada et al., "Compact full-field hard x-ray microscope based on advanced Kirkpatrick-Baez mirrors," Optica, vol. 7, No. 4 pp. 367-370 (2020).
Yashiro et al., "Optimal Design of Transmission Grating for X-ray Talbot Interferometer", Advances in X-ray Analysis vol. 49(3) (2006), pp. 375-379.
Yashiro et al., "Efficiency of capturing a phase image using cone-beam x-ray Talbot interferometry", J. Opt. Soc. Am. A vol. 25 (2008), pp. 2025-2039.
Yashiro et. al., "Hard-X-Ray Phase-Difference Microscopy Using a Fresnel Zone Plate and a Transmission Grating", Phys. Rev. Lett. vol. 103 (2009), 180801.

(56) References Cited

OTHER PUBLICATIONS

Yashiro et al., "Hard x-ray phase-imaging microscopy using the self-imaging phenomenon of a transmission grating", Phys. Rev. A vol. 82 (2010), 043822.
Yashiro et al., "On the origin of visibility contrast in x-ray Talbot interferometry", Opt. Express (2010), pp. 16890-16901.
Yashiro et al., "X-ray Phase Imaging Microscopy using a Fresnel Zone Plate and a Transmission Grating", in The 10th International Conference on Synchrotron Radiation Instrumentation, AIP Conf. Proc. vol. 1234 (2010), pp. 473-476.
Yashiro et al., "Distribution of unresolvable anisotropic microstructures revealed in visibility-contrast images using x-ray Talbot interferometry", Phys. Rev. B vol. 84 (2011), 094106.
Yashiro et al., "X-ray Phase Imaging and Tomography Using a Fresnel Zone Plate and a Transmission Grating", in "The 10th International Conference on X-ray Microscopy Radiation Instrumentation", AIP Conf. Proc. vol. 1365 (2011) pp. 317-320.
Yashiro et al., "Theoretical Aspect of X-ray Phase Microscopy with Transmission Gratings" in International Workshop on X-ray and Neutron Phase Imaging with Gratings, AIP Conf. Proc. vol. 1466, (2012), pp. 144-149.
Yoshioka et al., "Imaging evaluation of the cartilage in rheumatoid arthritis patients with an x-ray phase imaging apparatus based on Talbot-Lau interferometry," Scientific Reports, 10:6561, https://doi.org/10.1038/s41598-020-63155-9 (2020).
Zan et al., "High-resolution multicontrast tomography with an X-ray microarray anode-structured target source," PNAS, doi.org10.1073/pnas.2103126118 (2021).
Zanette et al., "Two-Dimensional X-Ray Grating interferometer," Phys. Rev. Lett. vol. 105 (2010) pp. 248102-1 248102-4.
Zeeshan et al., "In-house setup for laboratory-based x-ray absorption fine structure spectroscopy measurements," Rev. Sci. Inst. 90, 073105 (2019).
Zeng et al., "Glass Monocapillary X-ray Optics and Their Applications in X-Ray Microscopy," X-ray Optics and Microanalysis: Proceedings of the 20th International Congress, AIP Conf. Proc. vol. 1221, (2010), pp. 41-47.
Zhan et al., "A Lightweight Method for Detecting IC Wire Bonding Defects in X-ray Images," Micromachines, vol. 14, p. 1119, https://doi.org/10.3390/mi14061119 (2023).
Zhang et al., "Application of confocal X-ray fluorescence based on capillary X-ray optics in nondestructively measuring the inner diameter of monocapillary optics," Optics Comm. (2018) https://doi.org/10.1016/j.optcom.2018.11.064.
Zhang et al., "Measurement of the inner diameter of monocapillary with confocal X-ray scattering technology based on capillary X-ray optics," Appl. Opt. (Jan. 8, 2019), doc ID 351489, pp. 1-10.
Zhang et al., "Laboratory-scale X-ray absorption spectrometer with a cylindrical Johansson crystal analyzer," Nuclear Inst. And Methods in Physics Research, A (2023), doi: https://doi.org/10.1016/j.nima.2023.168067 (2023).
Zhou et al., "X-ray wavefront characterization with grating interferometry using an x-ray microfocus laboratory source," Proceedings, vol. 11492, Advances in Metrology for X-Ray and EUV Optics IX; 114920Q, https://doi.org/10.1117/12.2576152 (2020).
Zhao et al., "X-ray wavefront sensing and optics metrology using a microfocus x-ray grating interferometer with electromagnetic phase stepping," Appl. Phys. Lett. 120, 181105 (2022).
Zhu et al., "Optical Wafer Defect Inspection at the 10 nm Technology Node and Beyond," 2022 Int. Extrem. Manuf. In press https://doi.org/10.1088/2631-7990/ac64d7 (2022).
Andreyev et al., "Boosting the versatility of X-ray microscopes by using robotic arm sample holders," 13th Conf. on Ind. Comp. Tomography, doi.org/10.58286/29261 (2024).
Arsana et al., "Laboratory Liquid-Jet X-ray Microscopy and X-ray Fluorescence Imaging for Biomedical Applications," Int'l J. Mol. Sci., Vo. 25, p. 920 (2024).
Bertilson et al., "Analyzer-free Hard X-ray Interferometry," Phys. Med. Biol. https://doi.org/10.1088/1361-6560/ad1f84 (2024).
De Pauw et al., "A review of laboratory, commercially available, and facility based wavelength dispersive X-ray fluorescence spectrometers," J. Anal. At. Spectrom., doi: 10.1039/d3ja00315a (2023).
Gironda et al., "Asymmetric Rowland circle geometries for spherically bent crystal analyzers in laboratory and synchrotron applications," J. Anal. At. Spectrom., doi: 10.1039/d3ja00437f (2024).
Gu et al., "A Breakthrough in Resolution and Scan Speed: Overcome the Challenges of 3D X-ray Imaging Workflows for Electronics Package Failure Analysis," 2023 IEEE Int'l Symp. Phys. and Failure Analysis of Integrated Circuits (IPFA), doi: 10.1109/IPFA58228.2023.10249028 (2023).
Kutukova et al., "Laboratory High-Contrast X-ray Microscopy of Copper Nanostructures Enabled by a Liquid-Metal-Jet X-ray Source," Nanomaterials, vol. 14, p. 448 (2024).
Liao et al., "Design of a full-filled transmission X-ray microscope with 30nm resolution," SPIE Proc. Publ., ChinaXiv:202311.00232v1 (2023).
Lin et al., "High energy x-ray Talbot-Lau interferometer employing a microarray anode-structured target source to extend the field of view," Phys. Med. Biol., doi.org/10.1088/1361-6560/ad0196 (2023).
Lucht et al., "Phase retrieval beyond the homogeneous object assumption for X-ray in-line holographic imaging," arXiv:2403.00461v1 [eess.IV] (2024).
Momose et al., "Development of grating-based super-resolution x-ray phase imaging," AIP Conf. Proc. 2990, 030003 (2023).
Nakamura et al., "Nanoscale X-ray Tomography of Integrated Circuits using a Hybrid Electron/X-ray Microscope: Results and Prospects," 2023 IEEE Phys. Assurance and Inspection of Electron., doi: 10.1109/PAINE58317.2023.10318004 (2023).
Novichkov et al., "Laboratory-based X-ray spectrometer for actinide science," J. Synch. Rad. vol. 30, doi.org/10.1107/S1600577523006926 (2023).
Sefi et al., "25-Fold Resolution Enhancement of X-ray Microscopy Using Multipixel Ghost Imaging," arXiv:2402.14023 (2024).
Shimamura et al., "Soft X-ray nanobeams formed by aberration-reduced elliptical mirrors with large numerical aperture," Opt. Express, vol. 31, No. 23, 38132 (2023).
Six et al., "Joint multi-contrast CT for edge illumination X-ray phase contrast imaging using split Barzilai-Borwein steps," Op. Express, vol. 32, No. 2, pp. 1135-1150 (2024).
Su et al., "Quantitative Dual-Energy X-ray Imaging Based on K-Edge Absorption Difference," J. Phys. Chem. Lett. vol. 14, pp. 10074-10079 (2023).
Villarraga-Gómez et al., "Assessing Electronic Devices with Advanced 3D X-ray Imaging and Electron Microscopy" (2023).
Watts et al., "The development of laboratory-based high energy sources for XPS," Surf. Interface Anal., pp. 1-17, doi:10.1002/sia.7300 (2023).
Wirtensohn et al., "The Dark Side of Transmission X-Ray Microscopy," arXiv:2403. 18884v1 [physics.optics[ Mar. 27, 2024.
YUAN at al., "Micro X-ray fluorescence device based on monocapillary ellipsoidal lens for thin film thickness measurements," Nucl. Inst. Meth. Phys. Res. A, vol. 1058, p. 168923 (2024).
Zhao et al., "Applications of the non-negative least-squares deconvolution method to analyze energy-dispersive x-ray fluorescence spectra," Appl. Op., Vo 62, No. 20, pp. 5556-5564 (2023).

\* cited by examiner

SYSTEM AND METHOD FOR COMPACT LAMINOGRAPHY UTILIZING MICROFOCUS TRANSMISSION X-RAY SOURCE AND VARIABLE MAGNIFICATION X-RAY DETECTOR

CLAIM OF PRIORITY

This application claims the benefit of priority to U.S. Provisional Appl. No. 63/269,369 filed on Mar. 15, 2022 and incorporated in its entirety by reference herein.

BACKGROUND

Field

This application relates generally to laminography x-ray imaging systems.

Description of the Related Art

X-ray computed laminography (CL) is a method for three-dimensional imaging of samples having a high aspect ratio in three dimensions (e.g., substantially planar samples). CL is well suited for semiconductor samples, such as wafers and packages where the alternative for three-dimensional imaging computed tomography (CT) may not work well due to beam hardening and/or low contrast.

Commercial CL systems use a microfocus x-ray tube and a flat panel style detector that includes a scintillating screen, fiber optic plate, and pixel array sensor (see, e.g., Yxlon Cheetah EVO, Nikon XTV160, Nordson XM8000, Sec X-eye NF120, Omron VT-X900). Such a detector typically has pixel sizes in the range of 50-150 microns or greater and thick scintillator materials that are efficient at detecting x-rays at 100 kV or more. To achieve sub-micron effective pixel sizes, the relatively large pixels of the flat panel detector are used with large geometric magnifications (e.g., a geometric magnification of 200× used with a flat panel detector having pixels sizes of 100 microns can achieve an effective pixel size of 0.5 micron). If the region of interest of the sample being analyzed is placed 5 millimeters from the x-ray source, a sample-detector distance of one meter can provide a 200× magnification. This one meter sample-detector distance implies an overall system length of approximately two meters or more.

SUMMARY

In certain implementations, an x-ray computed laminography imaging system is configured to generate a transmission image of a region of interest of an object. The system comprises a transmission x-ray source configured to generate x-rays at an x-ray source focal spot. At least some of the x-rays propagate along an x-ray propagation axis extending from the x-ray source focal spot through the region of interest of the object. The system further comprises a stage assembly comprising at least one rotation stage configured to rotate the object about a rotation axis extending through the region of interest. The rotation axis is at an angle relative to the normal to the x-ray propagation axis in a range of 10 degrees to 60 degrees. The system further comprises at least one x-ray detector configured to intercept at least some of the x-rays propagating along the x-ray propagation axis. The at least one x-ray detector comprises at least one optical subsystem and a two-dimensional pixelated imaging circuitry comprising an imaging area configured to receive a two-dimensional image from the at least one optical subsystem. The at least one optical subsystem comprises a scintillator having a thickness that is substantially parallel to the x-ray propagation axis. The scintillator is configured to generate visible light in response to x-rays impinging the scintillator. The at least one optical subsystem further comprises at least one optical lens configured to receive the visible light from the scintillator and to focus the visible light into the two-dimensional image. The at least one optical lens has a depth of focus, and the thickness of the scintillator is in a range of 1 to 20 times the depth of focus.

In certain implementations, a method generates at least one two-dimensional image of a region of interest of an object. The method comprises emitting diverging x-rays from an x-ray source focal spot. The method further comprises propagating at least some of the x-rays along an x-ray propagation axis through the region of interest of the object. The method further comprises positioning the object at a plurality of rotational positions by rotating the object about a rotation axis extending through the region of interest. The rotation axis is at an angle relative to the normal of the x-ray propagation axis in a range of 10 degrees to 60 degrees. The method further comprises, for one or more of the rotational positions of the object, detecting x-rays that have propagated through the region of interest.

DETAILED DESCRIPTION

Figure 1:
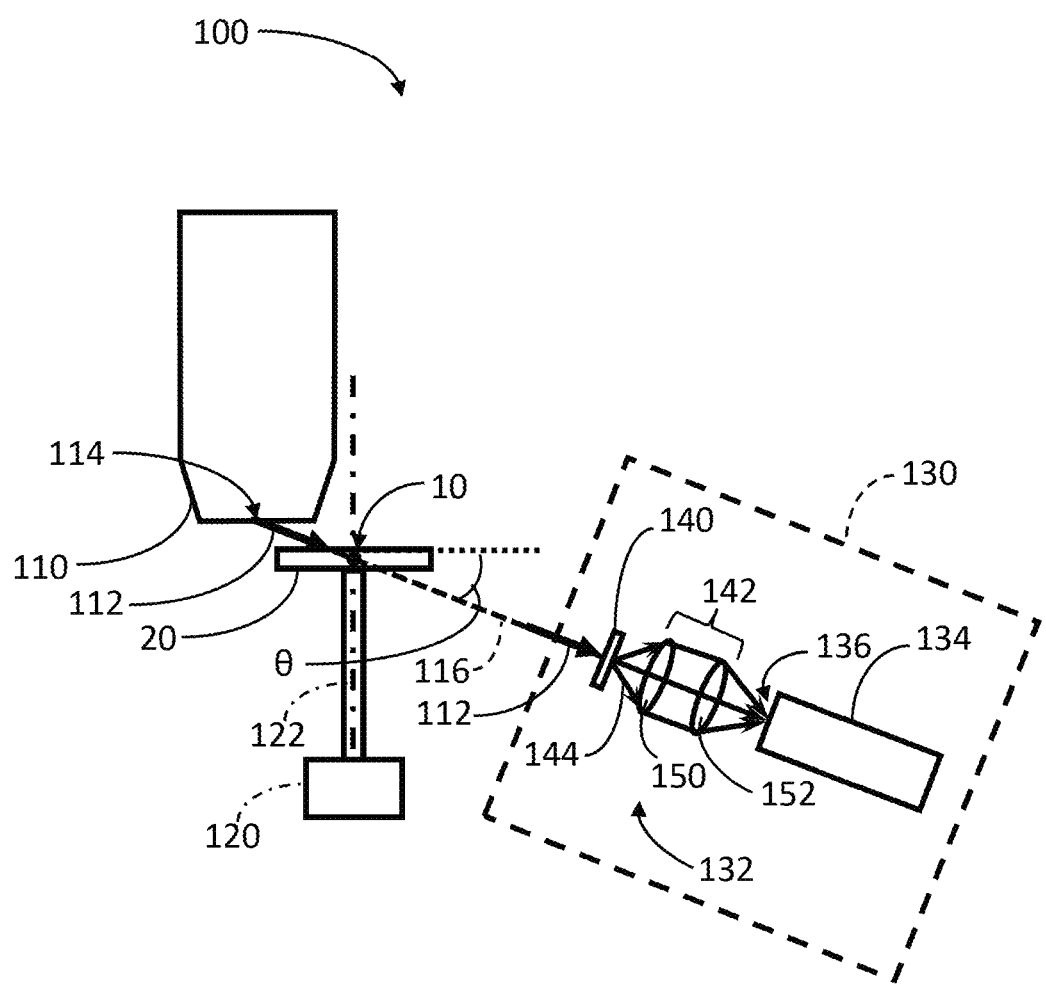
FIG. 1 schematically illustrates an example x-ray computed laminography imaging system in accordance with certain implementations described herein.

In contrast to conventional CL systems, certain implementations described herein utilize a detector with pixels having effective pixel sizes in a range of 0.3 micron to 20 microns (e.g., 0.3 micron to 5 microns, 5 microns to 20 microns), a geometric magnification in a range of 5× to 50× (e.g., 10× to 50×), and a sample-detector distance in a range of less than or equal to 1000 millimeters (e.g., 50 millimeters to 500 millimeters, 500 millimeters to 800 millimeters, 800 millimeters to 1000 millimeters). Certain such implementations provide a significant reduction in size and weight of the overall system as compared to conventional CL systems. For example, certain implementations described herein can be configured to both work in the described geometry and as a conventional x-ray microscope within the same system, the overall length of which can be limited to less than or equal to two meters to reduce the size of the system, reduce the weight from lead shielding (e.g., thereby enabling the system to fit in freight elevators and on trucks for transportation), or both. In addition, certain implementations described herein can provide a greater range of magnification, can provide a superior (e.g., smaller) effective pixel size to improve resolution, and/or can manipulate the detected x-ray spectrum to achieve higher contrast (e.g., by selecting scintillator materials that have spectral responses optimized for obtaining high image contrast). For example, the K absorption edges of Cs and I of a CsI scintillator can be used for their high stopping power for x-rays with energies in a range of 34 keV to 50 keV. For another example, the L or K absorption edges of a Lu-based scintillator can be used to detect x-rays with energies above the respective ionization energy over a portion of the energy band (e.g., about 40% of the ionization energy).

In conventional systems which utilize a flat panel style detector and a high geometric magnification, the source-sample distance is typically selected to be as small as possible (e.g., in a range of 1 millimeter to 10 millimeters) to achieve large image magnification. With a slant angle θ (e.g., the angle between the normal to the rotation axis and the x-ray propagation axis), the distance between the x-ray source and the region of interest (ROI) is equal to the product of the source-sample distance and $1/\sin(\theta)$. With a small slant angle (e.g., 10 degrees), the minimum sample-ROI distance can range from 6 millimeters to 60 millimeters with a source-sample distance of 1 millimeter to 10 millimeters. To achieve 0.25-micron pixel resolution in a ROI with a flat panel detector with 50-micron pixel size (e.g., currently the smallest pixel size commercially available for flat panel detectors) and a source-ROI distance of 6 millimeters (e.g., corresponding to a source-sample distance of 1 millimeter and a slant angle of 10 degrees), a minimum source to detector distance of 6*50/0.25=1200 millimeters would be used. For larger source-sample distances (e.g., 5 millimeters), the source-detector distances are much larger (e.g., 6000 millimeters and 2000 millimeters for slant angles of 10 degrees and 30 degrees, respectively). Therefore, it can be desirable to have detectors with small detector pixel sizes for source-sample distances in the range of 1 millimeter to 10 millimeters over slant angles in a range of 10 degrees to 30 degrees.

Furthermore, a small source-sample distance can suffer sample heating problems for certain applications. Only 0.1% of the total power delivered by the electron beam to the x-ray generating anode is converted to x-rays, with the remaining power being dissipated as heat. As a result, when the sample is placed close to the x-ray source for the small source-sample distance, the radiant heat from the x-ray generating anode heats the sample, resulting in thermal expansion of the sample and/or the sample mount during measurements and reduced image resolution and three-dimensional reconstruction fidelity. In contrast, certain implementations described herein utilize effective pixel sizes in the range of 0.3 micron to 5 microns (e.g., 0.3 micron to 1 micron, 1 micron to 5 microns, 5 microns to 20 microns) which is smaller than those of conventional systems (e.g., in the range of 50 microns to 200 microns), and the geometric magnification can be reduced such that the sample can be placed farther from the focal spot of the electron beam within the x-ray source (e.g., tube focus)(e.g., source-sample distance in a range of 1 millimeter to 50 millimeters (e.g., 1 millimeter to 5 millimeters, 5 millimeters to 20 millimeters, 20 millimeters to 50 millimeters), to reduce thermal heating (e.g., heat load) of the sample, thereby reducing the associated thermal instability and ameliorating image artifacts due to the thermal expansion, and/or to accommodate sample holders, dose-reducing masks or filters, and/or samples with features that cannot be removed (e.g., heat sinks, etc.).

The flat panel detectors used in conventional systems have relatively thick scintillators (e.g., thickness in a range of 200 microns to 700 microns) which have a much different x-ray absorption spectrum than do thin scintillators (e.g., thickness in a range of 10 microns to 200 microns (e.g., 10 microns to 40 microns, 40 microns to 80 microns, 80 microns to 200 microns). Relatively thin scintillators are used in scintillator coupled objective detector systems which have the full thickness of the scintillator within the depth of focus (DOF) of the objective to avoid blurring. In certain implementations, thin scintillators (e.g., thickness in a range of 10 microns to 50 microns) are used which have decreased efficiency for detecting higher energy x-rays but have higher efficiencies for detecting lower energy x-rays (e.g., with a greater contrast), such that thin scintillators act as high pass filters.

In addition, the source-sample distances of certain implementations described herein, which are larger than those of conventional laminography systems, advantageously allow the sample to be mounted on a rotation axis with the largest plane of the sample at an angle relative to the rotation axis (e.g., in a range of 1 degree to 80 degrees, 1 degree to 10 degrees, 10 degrees to 30 degrees, 30 degrees to 50 degrees, 50 degrees to 80 degrees), this angle being defined as the sample mounting tilt angle relative to the system's rotation axis, and that is larger than the laminography slant angle (e.g., the angle between the normal to the rotation axis and the x-ray propagation axis, as measured from the x-ray source to the detector). In certain implementations in which the diverging x-ray beam from the x-ray source has a cone-shaped spatial distribution, the x-ray propagation axis is the central axis of the cone shape. In certain implementations using an x-ray source comprising an x-ray transmissive vacuum window having an outer surface, the laminography slant angle can be substantially equal to the angle between the rotation axis and the outer surface of the vacuum window. For relatively small samples (e.g., largest dimension in the range of 1 millimeter to 5 millimeters, 5 millimeters to 10 millimeters, 10 millimeters to 100 millimeters), the sample can be mounted such that the rotation axis is substantially parallel to a direction along which the largest dimension of the sample corresponds like conventional computed tomography (CT). Using sample mounting tilt angles that are larger than the laminography slant angle, certain implementations described herein can capture Fourier space information during a measurement scan that would be otherwise missing from a conventional CL measurement scan, thereby reducing (e.g., eliminating) CL artifacts corresponding to the missing Fourier space information.

For CL imaging, it can be helpful to adjust the magnification of the system. For example, imaging with a large field of view can be used at the start to orient the sample and subsequent imaging that is zoomed in to a particular region of interest (ROI) can then be used. In conventional CL microscopes having a flat panel style detector, changing the magnification is performed by precisely translating the x-ray source, sample, and/or detector over relatively large distances, using precise and large staging that are capable of bearing the heavy and delicate loads. In contrast, certain implementations described herein utilizing detection systems having a CCD or CMOS sensor and a scintillating screen that converts x-rays to visible light that is coupled to either a visible light objective lens or a fiber optic plate to provide effective pixel sizes (e.g., widths in the range of 0.2 microns to 20 microns (e.g., 0.2 micron to 1 micron, 1 micron to 5 microns, 5 microns to 20 microns) that are smaller than the standalone pixel size of the CCD or CMOS sensor. Certain such implementations can enable overall higher resolution imaging without limiting the x-ray source by reducing the electron beam spot size or its concomitant power density limit. For example, the electron beam focus and the detector pixel size can be roughly equal and the geometric magnification can be set to about 2. Under such conditions, a spatial resolution higher than the typical 50% of the electron beam focal spot size can be achieved. In this way, certain implementations described herein achieve sub-micron spatial resolution in a CL system using a pixel size of a few microns, which is incompatible with commercially available flat panel style detectors.

Figure 2:
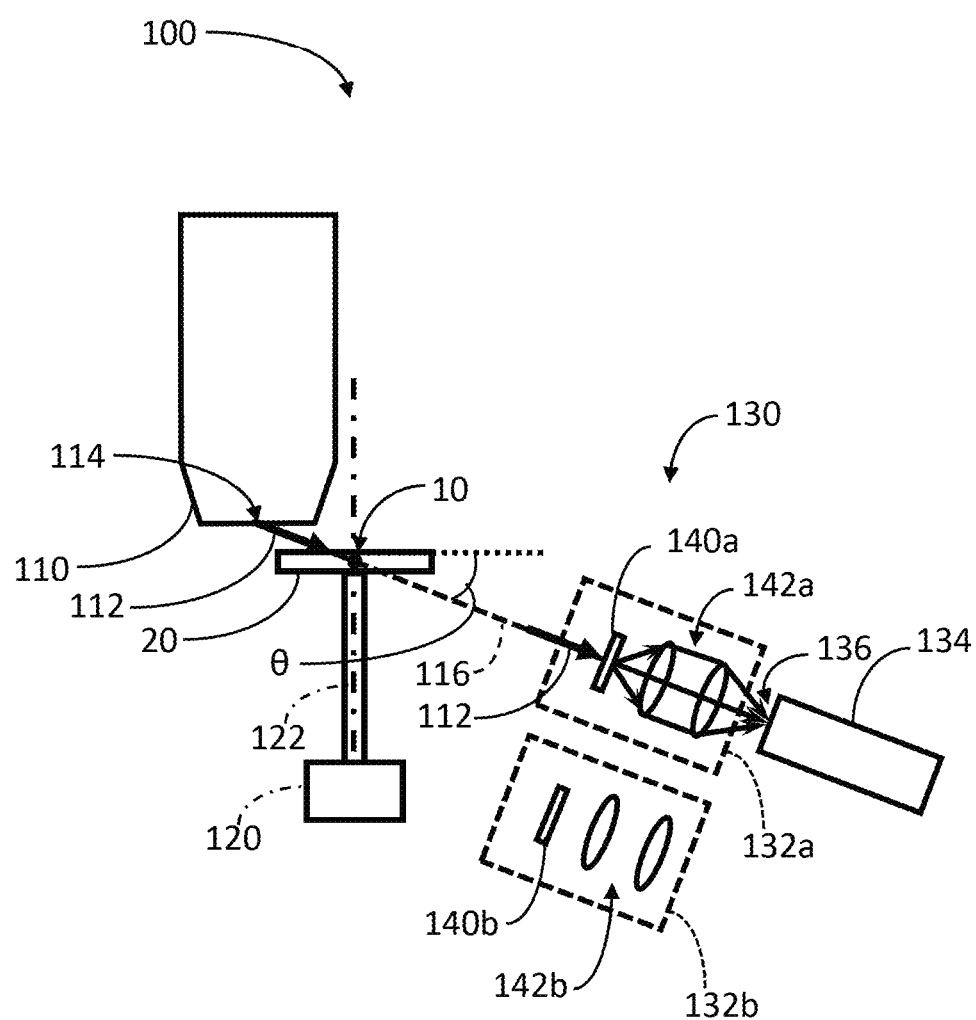
FIG. 2 schematically illustrates another example x-ray computed laminography imaging system in accordance with certain implementations described herein.

FIGS. 1 and 2 schematically illustrate two examples of an x-ray computed laminography imaging system 100 configured to generate a transmission image of a region of interest (ROI) 10 in an object 20 in accordance with certain implementations described herein. The system 100 comprises a transmission x-ray source 110 configured to generate x-rays 112 at an x-ray source focal spot 114. For example, the transmission x-ray source 110 can comprise a sealed tube that is not actively pumped. At least some of the x-rays 112 propagate along an x-ray propagation axis 116 (e.g., a central x-ray propagation axis of the x-rays 112 propagating in a cone-shaped spatial distribution) extending from the x-ray source focal spot 114 through the ROI 10 of the object 20. The system 100 further comprises at least one rotation stage 120 configured to rotate the object 20 about a rotation axis 122 extending through the ROI 10. The normal to the rotation axis 122 is at an angle θ relative to the x-ray propagation axis 116 in a range of 5 degrees to 60 degrees (e.g., 5 degrees to 10 degrees, 10 degrees to 30 degrees, 30 degrees to 45 degrees, 45 degrees to 60 degrees). The system 100 further comprises at least one x-ray detector 130 (e.g., at least one area detector) configured to intercept the x-rays 112 propagating along the x-ray propagation axis 116. The at least one x-ray detector 130 comprises at least one optical subsystem 132 and a two-dimensional pixelated imaging circuitry 134 (e.g., spatially-resolving camera) comprising an imaging area 136 (e.g., CCD sensor, CMOS sensor) configured to receive a two-dimensional image from the at least one optical subsystem 132. The at least one optical subsystem 132 comprises a scintillator 140 and an optical assembly 142 (e.g., at least one optical lens; a magnifying fiber optic plate). The scintillator 140 has a surface normal and a thickness that are substantially parallel to the x-ray propagation axis 116, and the scintillator 140 is configured to generate visible light 144 in response to x-rays 112 impinging the scintillator 140. The optical assembly 142 is configured to receive the visible light 144 from the scintillator 140 and to guide (e.g., focus) the visible light 144 into the two-dimensional image. The optical assembly 142 has a depth of focus (DOF), and the thickness of the scintillator 140 is in a range of 1 to 20 times (e.g., 1× to 20×, 1× to 5×) the DOF (e.g., substantially equal to an integer multiple of the DOF, the integer multiple in a range of 1 to 20 (e.g., 1 to 5).

In certain implementations, the object 20 (e.g., sample) is substantially planar (e.g., semiconductor wafer, semiconductor package, battery pouch cell) and is held by a sample mount such that the object 20 is substantially perpendicular to the rotation axis 122. For example, having the rotation axis 122 substantially parallel to the direction of gravity, holding the object to be substantially perpendicular to the rotation axis 122 can facilitate easier alignment of the ROI 10 of the object 20 onto the rotation axis 122 and can reduce (e.g., avoid) distortion of the object 20.

In certain implementations, the transmission x-ray source 110 comprises a microfocus or nanofocus transmission x-ray tube configured to emit x-rays 112 from a terminal face of the x-ray tube. The spot size of the x-ray source focal spot 114 can be in a range of less than or equal to 1 micron or in a range of 1 micron to 5 microns or in a range of 5 microns to 20 microns. In certain implementations, the distance between x-ray source focal spot 114 and the ROI 10 is in a range of less than or equal to 3 millimeters, in a range of 3 millimeters to 5 millimeters, or in a range of 5 millimeters to 10 millimeters. In certain implementations, the x-rays 112 generate are polychromatic and have a mean energy in a range greater than 10 keV (e.g., 10 keV to 30 keV, 30 keV to 80 keV, 80 keV to 140 keV). For example, the x-ray source 110 can comprise an x-ray generating target material comprising a metal layer (e.g., W, Mo, Rh, Au) on a diamond or beryllium exit window. The metal layer can have a thickness that is in a range of less than or equal to 8 microns (e.g., less than or equal to 1 micron, 1 micron to 2 microns, 2 microns to 3 microns, 3 microns to 8 microns). The metal layer thickness can be configured to minimize self-absorption resulting from the x-ray propagation axis 116 having a shallow angle relative to the outer surface of the metal layer, thereby significantly increasing the pathlength of the x-ray beam through the metal layer. In certain implementations, the exit window has a thickness in a range of 10 microns to 1500 microns (e.g., 10 microns to 50 microns, 50 microns to 500 microns, 500 microns to 1500 microns). In certain implementations, the x-ray source 110 comprises more than one region of x-ray generating material, such as regions of different x-ray generating metal layer thicknesses and/or regions of different x-ray generating metal materials. In certain implementations, the target of the x-ray source 110 comprises additional layers (e.g., layers that comprise Ir, TiN, TiC, etc.) that provide various functionalities (e.g., adhesion, reduced thermal resistivity, anti-diffusion) between the x-ray generating metal layer and the exit window. The x-ray source 110 of certain implementations is configured such that the angle between the exit window surface and the x-ray propagation axis 116 is in a range of −5 degrees (e.g., tilted towards the exit window surface by 5 degrees) to 45 degrees (e.g., tilted away from the exit window surface by 45 degrees). For example, the angle can be in a range of 0 (e.g., parallel to the exit window surface) to 30 degrees (e.g., tilted away from the exit window surface by 30 degrees).

As schematically illustrated by FIG. 1, the x-ray source 110 can have a substantially planar surface through which the generated x-rays 112 are emitted (e.g., the exit window), and the planar surface can face and can be positioned substantially parallel to an outer substantially planar surface of the object 20. For example, an angle between the planar surface of the object 20 and the substantially planar surface of the x-ray source 110 can be in a range of 0 to 5 degrees of parallel, a range of 0 to 10 degrees of parallel, a range of 0 to 20 degrees of parallel, or in a range of 0 to 45 degrees of parallel. The spatial distribution of emitted diverging x-rays 112 can have a cone shape (e.g., angular divergence greater than 30 degrees) and a central axis (e.g., a cone with a central axis that is 170 degrees from the substantially planar surface of the x-ray source 110), the central axis equivalent to the x-ray propagation axis 116, which can be defined as the line extending from the x-ray source focal spot 114 to a center of the imaging area 136. A portion of the x-rays 112 propagate through the object 20 and the ROI 10, and are incident on the scintillator 140 of the at least one x-ray detector 130.

In certain implementations, the system 100 further comprises a gap sensor subsystem configured to monitor a spacing (e.g., gap) between the substantially planar surface through which the generated x-rays 112 are emitted (e.g., the exit window) and the substantially planar surface of the object 20. For example, the sensor subsystem can comprise one or more laser sources and one or more optical sensors (e.g., a safety laser scanner; an area-type laser sensor or curtain). Such a sensor subsystem can be configured to trigger and/or stop one or more motorized linear stages configured to move the x-ray source 110 and/or the object 20 to maintain the spacing between the exit window and the object 20 at a predetermined distance and/or to ensure that the spacing is not less than a predetermined gap limit. In certain implementations, the predetermined gap limit is in a range less than or equal to 1 millimeter (e.g., less than or equal to 100 microns, 100 microns to 300 microns, 300 microns to 500 microns).

In certain implementations, the system 100 further comprises a visible light camera configured to be placed above the object 20 along the rotation axis 122 of the rotation stage 120 and focused on a portion of the object 20 aligned with the ROI 10 along the rotation axis 122. For example, the camera can have a focal point that is in a range of 1 millimeter to 10 millimeters (e.g., 5 millimeters) below the substantially planar surface of the object 20. In certain implementations, the camera can be configured to be moved into position above the object 20 after the x-ray source 110 is moved away from the object 20 so as to make room for the camera. The camera can be configured to optically monitor a position of a selected ROI 10 relative to the rotation axis 122 as the object 20 is moved into position to facilitate correct positioning of the ROI 10 on the rotation axis 122.

In certain implementations, the system 100 further comprises an infrared shield configured to be placed between the substantially planar surface through which the generated x-rays 112 are emitted (e.g., the exit window) and the substantially planar surface of the object 20. The infrared shield can be configured to reduce (e.g., minimize) the amount of heat from the x-ray source 110 reaching the object 20. In certain implementations, the system 100 further comprises a radiation shield (e.g., mask) configured to be placed between the substantially planar surface through which the generated x-rays 112 are emitted (e.g., the exit window) and the substantially planar surface of the object 20. The radiation shield can be configured to reduce (e.g., minimize) the amount of potentially damaging radiation (e.g., low energy x-rays) from the x-ray source 110 reaching other portions of the object 20 besides the ROI 10. The radiation shield can comprise a highly x-ray absorbing plate with one or more patterned recesses (e.g., holes) on or through the plate such that only one or more regions of the object 20 (e.g., test patters; scribe lines on a semiconductor wafer) are imaged. The radiation shield can have a minimum thickness in a range of less than or equal to 2 millimeters (e.g., less than or equal to 100 microns, 100 microns to 500 microns, 500 microns to 2 millimeters). In certain implementations, the system 100 further comprises a magnetic shield (e.g., comprising "mu-metal") configured to reduce (e.g., minimize) changes of the magnetic fields resulting from movements of other portions of the system 100 (e.g., the object 20) from reaching the electron beam within the x-ray source 110. The magnetic shield can comprise mu-metal (e.g., a nickel-iron alloy) and can be configured to substantially surround selected components (e.g., motors; permanent magnets of motors of the sample stage assembly) that produce magnetic fields.

In certain implementations, the rotation stage 120 comprises an air bearing or oil bearing rotary stage. The rotation stage 120 can have a small wobble (e.g., in a range of less than or equal to 50 microradians (e.g., 20 microradians to 50 microradians, 10 microradians to 20 microradians, less than or equal to 10 microradians, or less than or equal to 1 microradian) and a runout that is less than or equal to 5 microns (e.g., less than or equal to 1 micron, less than or equal to 500 nanometers). The plane normal to the rotation axis 122 can intersect the x-ray propagation axis 116 at an angle θ relative to the x-ray propagation axis 116 (e.g., in a range less than or equal to 45 degrees; in a range less than or equal to 30 degrees; in a range less than or equal to 20 degrees; in a range less than or equal to 10 degrees; in a range of 10 degrees to 45 degrees). In certain implementations (e.g., for computed tomography), the rotation axis 122 is substantially perpendicular to the substantially planar surface of the exit window of the transmission x-ray source 110 (e.g., having an angle relative to the normal of the exit window that is greater than or equal to 45 degrees, greater than or equal to 70 degrees, greater than or equal to 80 degrees). In certain implementations, the rotation stage 120 is a component of a sample stage that can accommodate a 300-millimeter diameter wafer. The sample stage can further comprise XYZ positioning stages that are placed on the rotation stage 120 and/or within a central aperture of the rotation stage 120. The X and Y positioning stages can move the object 20 along distances that are greater than or equal to 100 millimeters (e.g., 100 millimeters to 300 millimeters, 300 millimeters to 600 millimeters).

In certain implementations, the x-ray source 110 and the x-ray detector 130 are fixed in position during a 3D x-ray image acquisition, while the rotation stage 120 rotates the object 20. In certain implementations, a wafer alignment tool and a robotic exchanger are used to first pre-align a wafer sample to fiducials prior to placing the wafer on the sample mount, thereby allowing high-throughput 3D imaging of semiconductor wafers.

In certain implementations, the optical assembly 142 of the at least one optical subsystem 132 comprises a single lens (e.g., a microscope objective lens) configured to receive at least a portion of the visible light 144 from the scintillator 140 and to focus the two-dimensional image on the imaging area 136 of the spatially-resolving imaging circuitry 134. In certain other implementations, the optical assembly 142 comprises a plurality of lenses (e.g., an objective lens 150 and a tube lens 152, as schematically illustrated by FIG. 1; a plurality of objective lenses), the objective lens 150 is configured to receive at least a portion of the visible light 144 from the scintillator 140 and the tube lens 152 is configured to receive at least a portion of the visible light 144 from the objective lens 150, the tube lens 152 configured to focus the two-dimensional image at the imaging area 136 of the imaging circuitry 134. In certain implementations, the numerical aperture of the visible light lenses are in the range of 0.1 to 0.9 (e.g., 0.1 to 0.25, 0.25 to 0.5, 0.5 to 0.9). Examples of working distances of the objectives include 0.5 millimeter to 2 millimeters, 2 millimeters to 5 millimeters, and 5 millimeters to 30 millimeters. In certain implementations, the objective is infinity-corrected, and the scintillator is positioned substantially at the front focal point of the objective such that parallel rays are produced. The tube lens 152 can focus the parallel rays onto the imaging circuitry 134. The optical assembly 142 can be configured to project a magnified image from the scintillator 140 onto the imaging area 136 of the imaging circuitry 134. For example, the scintillator 140 can be placed at a focus of the optical assembly 142 to provide an optical magnification in the range of 4× to 40× (e.g., 4× to 10×; 10× to 40×; 10× to 30×; 20× to 30×; 20× to 40×).

In certain implementations, the two-dimensional image formed by the scintillator 140 and the optical assembly 142 at the imaging area 136 of the imaging circuitry 134 has an optical magnification in a range of 4× to 50×, with a resulting effective pixel size in a range between 0.1 micron to 10 microns, in which effective pixel size is defined as the intrinsic pixel size of the imaging sensor divided by the optical magnification of the objective lens. For example, for a CCD sensor with an intrinsic pixel size of 13 microns and an objective lens with a magnification of 10×, the effective pixel size is 1.3 microns. In certain implementations in which the effective pixel size is in the range between 0.1 micron to 10 microns, the system geometry is configured such that geometric magnification is relatively low (e.g., in a range of 1.1× to 3×) as compared to a projection-based 3D x-ray micro imaging system using a flat panel (e.g., geometric magnification greater than 10× to 100×) for high spatial resolution, which in turn allows the system 100 to have an overall system length that is more compact than conventional flat panel configurations with high geometric magnification.

In certain implementations, as schematically illustrated by FIG. 1, the at least one x-ray detector 130 comprises a single optical subsystem 132 comprising a scintillator 140 and an optical assembly 142 configured to generate the two-dimensional image at the imaging area 136 of the imaging circuitry 134. In certain other implementations, the at least one x-ray detector 130 comprises a plurality of optical subsystems 132, and each optical subsystem 132 comprises a scintillator 140 and an optical assembly 142. For example, as schematically illustrated by FIG. 2, the at least one x-ray detector 130 comprises two optical subsystems 132a,b that are configured to be selectively moved into position such that only one of the two optical subsystems 132a,b is configured to generate the two-dimensional image at the imaging area 136 of the imaging circuitry 134 at a time. In certain other implementations, the at least one x-ray detector 130 comprises more than two optical subsystems 132.

In certain implementations, the optical assembly 142 of the at least one optical subsystem 132 has a depth of focus (DOF) that is substantially equal to the wavelength λ of the optical light 144 divided by the square of the numerical aperture (NA) (DOF=λ/NA²). The thickness of the scintillator 140 is in a range of 1 to 20 times the DOF. For example, the thickness of the scintillator 140 can be substantially equal to n*DOF, where n=1, 2, 3, 4, or 5.

In certain implementations, the scintillator 140 of the at least one optical subsystem 132 comprises cesium iodide (e.g., doped with thallium), amorphous selenium, YAG (yttrium-aluminum-garnet), or lutetium-aluminum-garnet (LuAG) and the scintillator 140 can be prepared (e.g., thinned and polished, grown, or evaporated) to be substantially planar and to have a thickness in a range of less than 100 microns, less than 60 microns, or less than 30 microns. In certain implementations, the material of the scintillator 140 and the thickness of the scintillator 140 are selected to at least partially control the wavelength range of the x-rays 112 that are detected by the at least one x-ray detector 130. For example, absorption edges, mass densities, and atomic numbers of the scintillator material can influence the x-ray absorption spectrum of the scintillator 140. Photoelectric absorption contrast decreases with the cube of the x-ray energy, so in certain implementations, the relative sensitivity to lower energy x-rays 112 can be increased by selecting the thickness of the scintillator 140.

In certain such implementations, the different optical subsystems 132 of the plurality of optical subsystems 132 are configured to provide different optical magnifications to provide variable optical attributes for the system 100, such that selection of which optical subsystem 132 is used allows a choice of magnification, numerical aperture, scintillator thickness or material, or other attributes that can be desirable to control. For example, referring to FIG. 2, a first optical subsystem 132a can comprise a first scintillator 140a and a first optical assembly 142a that are configured to be translated into position to intercept the x-rays 112 and to provide a first optical magnification for the two-dimensional image formed at the imaging area 136 of the imaging circuitry 134. A second optical subsystem 132b can comprise a second scintillator 140b and a second optical assembly 142b that are configured to be translated into position to intercept the x-rays 112 and to provide a second optical magnification for the two-dimensional image formed at the imaging area 136 of the imaging circuitry 134, the second optical magnification different from the first optical magnification. The attributes of the scintillator 140 and/or of the optical assembly 142 of each optical subsystem 132 (e.g., scintillator thickness; visible light emission wavelengths; objective lens frequency response) can be configured to optimize performance of the optical subsystem 132 (e.g., to select an optical magnification and/or a numerical aperture of the optical subsystem 132 intercepting the x-rays 112).

In certain implementations, the optical subsystem 132 further comprises at least one x-ray absorber (e.g., x-ray grating) between the scintillator 140 and the ROI 10. The at least one x-ray absorber can be configured to modify the modulation transfer function (MTF) of the optical subsystem 132. In certain implementations, the optical subsystem 132 further comprises at least one x-ray filter between the scintillator 140 and the ROI 10. The at least one x-ray filter can be configured to absorb x-rays 112 having energies within at least one predetermined range to increase the contrast seen by the at least one x-ray detector 130.

In certain implementations, the at least one x-ray detector 130 comprises at least one stage (not shown) configured to move (e.g., adjust; translate; rotate) the at least one optical subsystem 132 into position to receive the x-rays 112 and to provide the visible light 144 to the imaging circuitry 134. For example, the at least one stage can be configured to place a selected optical subsystem 132 of a plurality of optical subsystems 132 (e.g., either a first optical subsystem 132a or a second optical subsystem 132b, as shown in FIG. 2) into the position (e.g., to change between scintillator and optical lens pairs), thereby allowing the system 100 to provide variable optical attributes (e.g., different optical magnifications). The at least one stage can comprise one or more actuators (e.g., manually driven; automatically driven by one or more motors) and can provide linear motion (e.g., the at least one optical subsystem 132 mounted on a rail) and/or rotational motion (e.g., the at least one optical subsystem 132 mounted on a rotatable turret, similar to a visible light microscope).

In certain implementations, the imaging circuitry 134 (e.g., camera) comprises a CCD sensor or a CMOS sensor (e.g., a 2 k×2 k CMOS sensor). The imaging area 136 of the imaging circuitry 134 can be pixelated with pixels having sizes in a range of 2 microns to 100 microns (e.g., 2 microns to 10 microns, 10 microns to 20 microns, 20 microns to 50 microns, 50 microns to 100 microns). The imaging circuitry 134 can be in operable communication with a computer system or other circuitry configured to record, analyze, manipulate, and/or output the two-dimensional image at the imaging area 136 of the imaging circuitry 134.

In certain implementations, the at least one optical subsystem 132 and the imaging circuitry 134 are configured to provide a magnified (e.g., effective) pixel size in the range of 0.25 micron to 10 microns. The effective pixel size, when back projected at the ROI 10 of the object 20, is configured to be comparable (e.g., within ±10%; within ±20%; within ±30%) of the electron beam focal spot size of the x-ray source 110. In certain such implementations, the magnified pixel size is configured to achieve high spatial resolution by using a geometric magnification (e.g., in the range of 1× to 100×) that is smaller than conventional CL systems, thereby reducing (e.g., minimizing) the overall system size.

Figure 3:
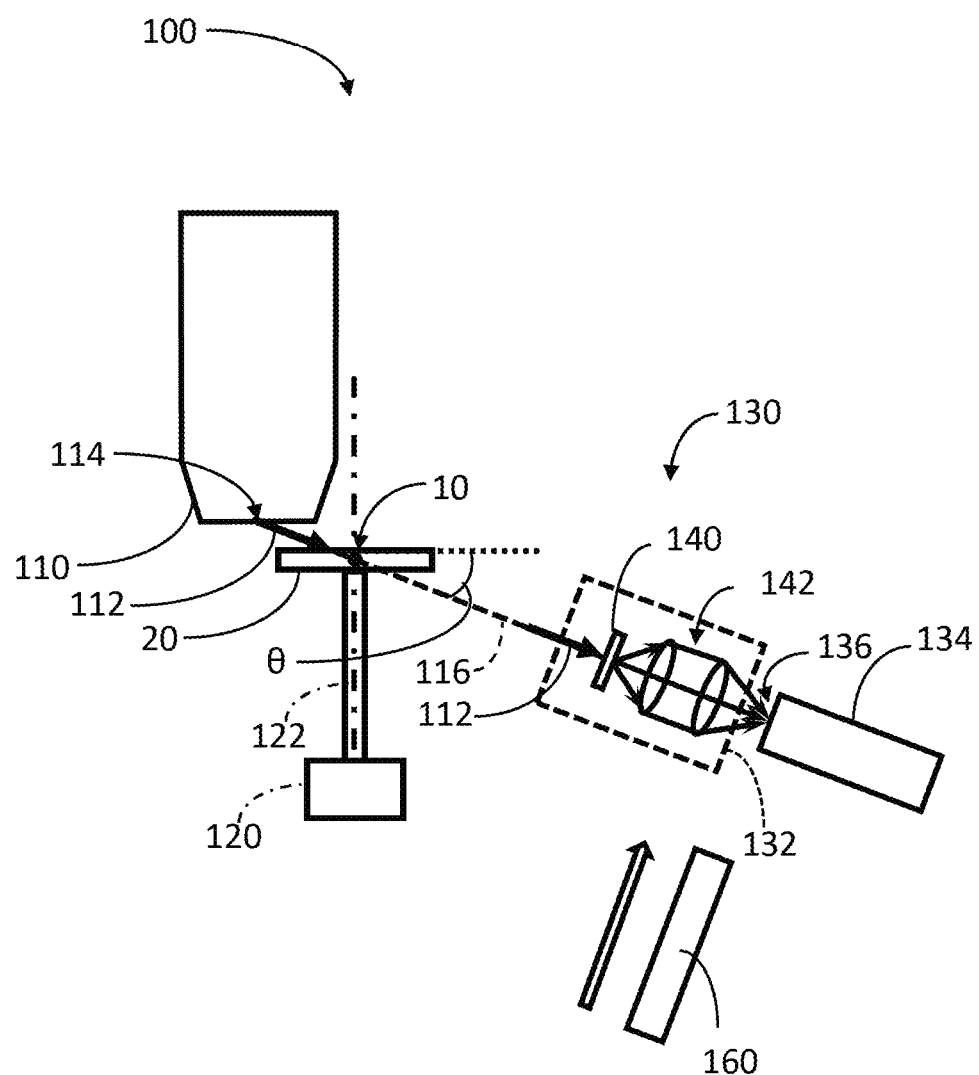
FIG. 3 schematically illustrates another example x-ray computed laminography imaging system 100 in accordance with certain implementations described herein.

FIG. 3 schematically illustrates another example x-ray computed laminography imaging system 100 in accordance with certain implementations described herein. The at least one x-ray detector 130 of FIG. 3 further comprises a second x-ray detector 160 (e.g., a flat panel detector; an amorphous selenium detector; a photon counting detector, an example of which is the Eiger2 x-ray detector from Dectris AG of Switzerland) that is configured to be moved (e.g., translated; adjusted) in place of a first x-ray detector (e.g., an objective-based detector comprising the scintillator 140, the at least one optical subsystem 132, and the imaging circuitry 134), such that the second x-ray detector 160 is configured to receive the x-rays 112 instead of the first x-ray detector receiving the x-rays 112 (e.g., the first x-ray detector and the second x-ray detector 160 are used mutually exclusively to one another). For example, the first x-ray detector and the second x-ray detector 160 can be mounted on at least one stage (not shown) configured to selectively switch between the first x-ray detector and the second x-ray detector 160 receiving the x-rays 112. The second x-ray detector 160 can have a larger pixel size than does the first x-ray detector and/or can comprise a scintillator or converter material having a thickness (e.g., greater than or equal to 120 microns, in a range of 200 microns to 1000 microns). The thickness of the scintillator or converter material of the second x-ray detector 160 can be larger than the thickness of the scintillator or converter material of the first x-ray detector. The second x-ray detector 160 of certain implementations is energy discriminating, while in certain other implementations, the second x-ray detector 160 is not energy discriminating.

Figure 4A:
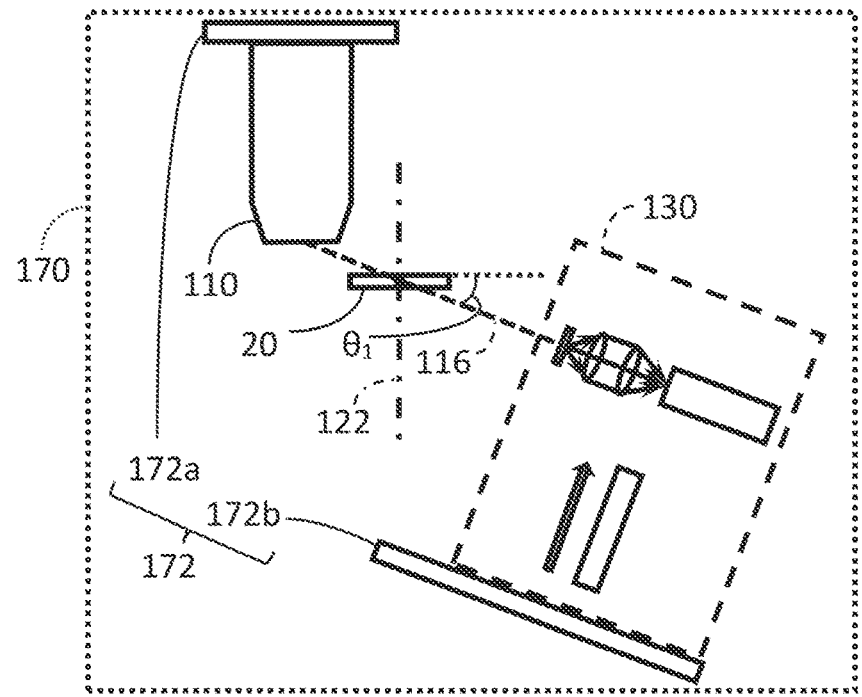
FIGS. 4A and 4B schematically illustrate another example x-ray computed laminography imaging system in accordance with certain implementations described herein.
Figure 4B:
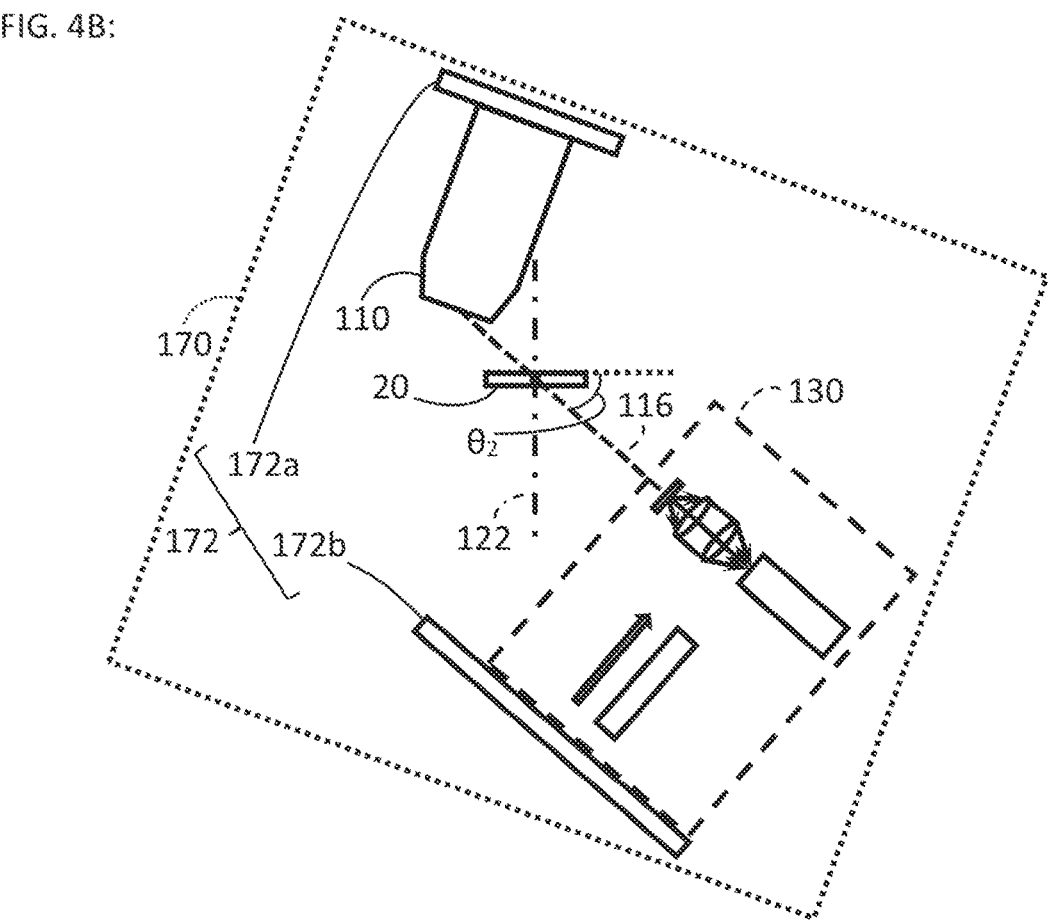

FIGS. 4A and 4B schematically illustrate another example x-ray computed laminography imaging system 100 in accordance with certain implementations described herein. The x-ray source 110 and the at least one x-ray detector 130 of FIGS. 4A and 4B are mounted on a motorized gantry 170 (e.g., having a rotating arm) configured to rotate the x-ray source 110 and the at least one x-ray detector 130 about a rotation pivot point at the intersection of the x-ray propagation axis 116 and the rotation axis 122. The gantry 170 is configured to vary the angle of the x-ray propagation axis 116 relative to the rotation axis 122 (e.g., the laminography slant angle $\theta$). For example, in FIG. 4A, the laminography slant angle is $\theta_1$ and in FIG. 4B, the laminography slant angle is $\theta_2$, with $\theta_1 < \theta_2$. In certain implementations, the laminography slant angle is configured to be changed between two different values selected from a range of 5 degrees to 45 degrees (e.g., 15 degrees to 30 degrees). The gantry 170 is further configured to keep a front face of the at least one x-ray detector 130 normal to the x-ray propagation axis 116 (e.g., with the imaging area 136 of the imaging circuit 134 normal to the x-ray propagation axis 116). In certain implementations, the gantry 170 is configured to vary the laminography slant angle $\theta$ to enable optimization of the measurements and to allow the balancing of reconstruction artifacts with higher throughput (e.g., depending on the measurement requirements). In certain implementations, the at least one x-ray source 110 is mounted on a goiniometer. The x-ray source 110 and the x-ray detector 130 can have sufficient motion such that they can be positioned so that the x-ray propagation axis 116 is orthogonal to the rotation axis 122 (e.g., for tomography image acquisition). In certain implementations, the system 100 is configured to alternate between tomography image acquisition and laminography image acquisition. In certain implementations, the ROI 10 of the object 20 is a fixed pivot point of the gantry 170, around which the x-ray source 110 and the x-ray detector 130 can be moved.

In certain implementations, the gantry 170 comprises a first track (e.g., rail) along which the x-ray source 110 can be moved and a second track (e.g., rail) along which the x-ray detector 130 can be moved. The first and second tracks can each be substantially circular arc sections with the first track having a first radius of curvature and the second track having a second radius of curvature, both the first and second radii of curvature centered on the ROI 10 of the object 20. The movement of the x-ray source 110 along the first track and of the x-ray detector 130 along the second track can be coordinated with one another to vary the laminography slant angle $\theta$ while the x-ray propagation axis 116 continues to extend through the ROI 10.

In certain implementations, the x-ray source 110 and/or the at least one x-ray detector 130 is mounted on a corresponding motorized stage 172 (e.g., at least one linear motion stage) that is configured to vary the geometric magnification of the system 100 by changing the distance between the x-ray source focal spot 114 and the ROI 10 and/or the distance between the ROI 10 and the at least one x-ray detector 130. For example, the geometric magnification can be varied in a range of 1.1× to 2×, a range of 2× to 10, in a range of 1× to 100×, or in a range of 1× to 200×. In certain implementations, the movements of the x-ray source 110 and the at least one x-ray detector 130 occur simultaneously and are coordinated with one another, while in certain other implementations, the movements of the x-ray source 110 and the at least one x-ray detector 130 are independent of one another. In certain implementations, the x-ray source 110 comprises one or more motorized stages 172a that allow translation of the x-ray source 110 along the x-ray propagation axis 116 passing through the ROI 10 to the at least one x-ray detector 130 (e.g., to the center of the at least one x-ray detector 130). In certain implementations, the x-ray detector 130 comprises one or more motorized stages 172b that allow translation of the x-ray detector 130 along the x-ray propagation axis 116.

Figure 5A:
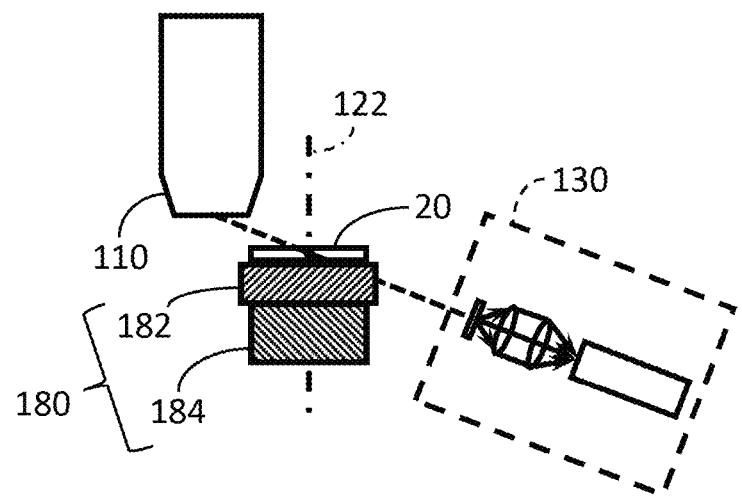
FIGS. 5A-5C schematically illustrate various examples of the system configured to collect x-ray projection images of the ROI through at least 300 degrees of sample rotation in accordance with certain implementations described herein.
Figure 5B:
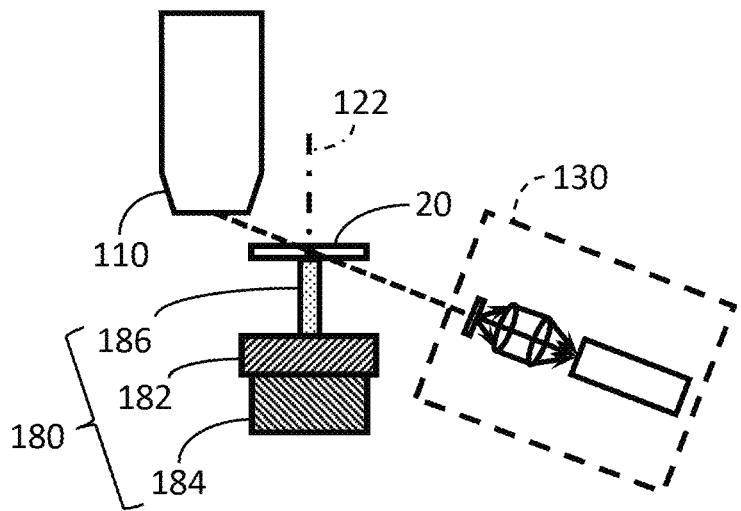
Figure 5C:
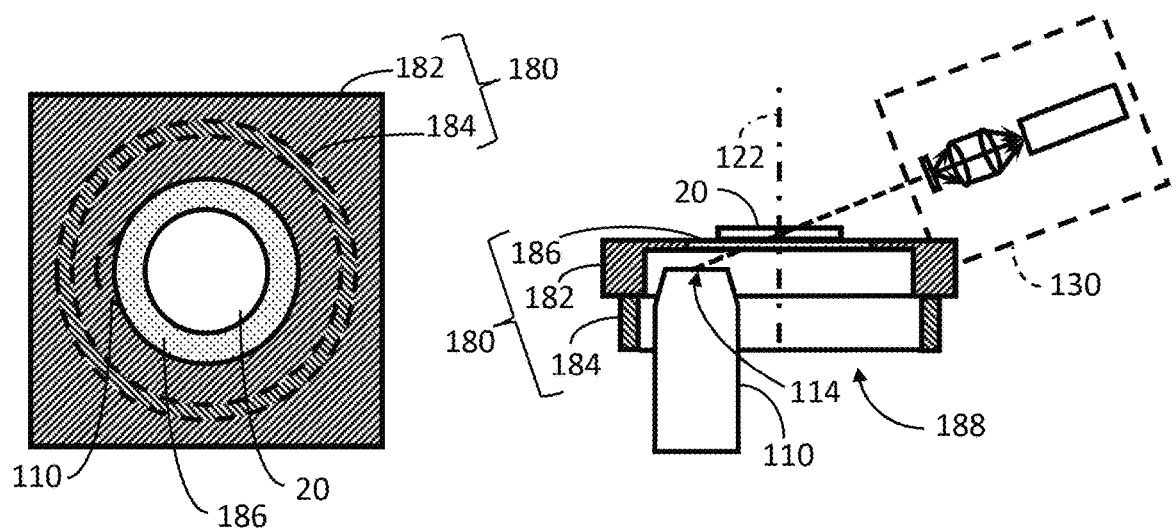

FIGS. 5A-5C schematically illustrate various examples of the system 100 configured to collect x-ray projection images of the ROI 10 through at least 300 degrees of sample rotation (e.g., 360 degrees) in accordance with certain implementations described herein. As schematically illustrated by FIG. 5A, the object 20 is mounted on a stage assembly 180 comprising at least one linear translation stage 182 (e.g., having up to three degrees of translation to position the ROI 10 at the rotation axis 122 for imaging) on a rotation stage 184 (e.g., rotatable about at least the rotation axis 122). In certain such implementations, at some laminography slant angles, because the object 20 is thin and is mounted on the at least one linear translation stage 182, the x-rays 112 propagating from the ROI 10 to the at least one x-ray detector 130 impinge the stage assembly 180 and are strongly attenuated by absorption by the stage assembly 180 (e.g., the motorized actuators, bracketry, and other portions of the stage assembly 180 are at least partially opaque to the x-rays 112). The attenuation of the x-rays 112 by the stage assembly 180 as the object 20 is rotated through the angular range of measurements (e.g., occlusion of at least some of the x-rays 112 from reaching the at least one x-ray detector 130) can introduce artifacts into the projection image which degrade the reconstruction fidelity.

As schematically illustrated by FIG. 5B, the stage assembly 180 comprises a support 186 (e.g., pedestal) between the object 20 and the other portions of the stage assembly 180 (e.g., the at least one linear translation stage 182 and the rotation stage 184). The support 186 is configured to hold the object 20. In certain implementations, the support is substantially transparent to a substantial fraction of the x-rays 112 (e.g., having greater than 50% transmission to x-rays 112 having x-ray energies greater than 50% of the acceleration voltage of the x-ray source 110). For example, the support 186 can be comprised essentially of low Z elements (e.g., atomic elements having atomic numbers less than 14) and/or can have thin portions (e.g., thickness along the rotation axis 122 less than 10 millimeters). In certain implementations, the support is configured to offset the object 20 from the rotation stage 120 by a predetermined distance in a range of 5 centimeters to 50 centimeters (e.g., 5 centimeters to 10 centimeters, 10 centimeters to 50 centimeters) such that the x-ray propagation axis 116 does not intersect the rotation stage 184. In certain implementations, the sample mount comprises a planar substrate at the top of the support 186 configured to hold the object 20. The planar substrate can have a transmittance greater than or equal to 30% to x-rays having energies above 10 keV in at least the ROI 10 of the object 20. The planar substrate can consist substantially (e.g., greater than 50%) of atomic elements with atomic numbers less than or equal to 20 (e.g., carbon fiber, boron nitride, silicon nitride, silicon, etc.). For laminography slant angles in a range of 10 degrees to 45 degrees (e.g., in a range of 10 degrees to 30 degrees), the support 186 separates the object 20 from the other portions of the stage assembly 180 such that the x-rays 112 propagating from the ROI 10 to the at least one x-ray detector 130 either do not impinge the support 186 or the other portions of the stage assembly 180 or are not substantially attenuated by absorption by the support 186 or the other portions of the stage assembly 180 (e.g., providing a mostly uniform absorption profile before impinging the at least one x-ray detector 130). In certain such implementations, the support 186 is configured to offset (e.g., separate) the rotation and translation actuation mechanisms of the stage assembly 180 from the beam cone of the diverging x-rays 112 for at least 300 degrees of rotation of the object 20 about the rotation axis 122.

FIG. 5C schematically illustrates a top view and a side cross-sectional view of an example system 100 having a stage assembly 180 at least partially bounding a substantially hollow volume 188 containing the x-ray source focal spot 114 in accordance with certain implementations described herein. As schematically illustrated by FIG. 5C, the x-ray source 110 and the stage assembly 180 are on the same side of the object 20 and the at least one x-ray detector 130 is on the opposite side of the object 20. The x-ray source 110 extends into the volume 188 (e.g., central aperture) at least partially bounded by the at least one linear translation stage 182 and the rotation stage 184. The volume 188 is sufficiently large to accommodate the x-ray source 110 while the object 20 is rotated about the rotation axis 122 by the rotation stage 184. The stage assembly 180 further comprises a support 186 (e.g., plate) that is configured to hold the object 20 on the stage assembly 180, the support 186 substantially transparent to a substantial fraction of the x-rays 112 (e.g., having greater than 50% transmission to x-rays 112 having x-ray energies greater than 50% of the acceleration voltage of the x-ray source 110). For example, the support 186 can be comprised essentially of low Z elements (e.g., atomic elements having atomic numbers less than 14) and/or thin materials (e.g., thickness along the rotation axis 19 less than 10 millimeters). At least some portion of the x-rays 112 from the x-ray source 110 travel first through the support 186, then through the ROI 10, and then impinge on the at least one x-ray detector 130. In certain implementations, the at least one linear translation stage 182 and the rotation stage 184 are kept from intersecting the x-ray cone of the x-rays 112 by having the x-ray source 110 inside the volume 188. In certain implementations, the hollow volume 188 is configured to permit integration of a metrology system (e.g., an optical microscope) for monitoring and aligning the object 20 relative to the x-ray source 110 and the at least one x-ray detector 130.

While FIG. 5C shows an example implementation in which the x-ray source 110 is below the object 20 and the at least one x-ray detector 130 is above the object 20, in other implementations, the x-ray source 110, the object 20, the at least one x-ray detector 130, and the stage assembly 180 can have any orientation while retaining the same relative positioning to one another. In certain such implementations, the object 20 can rotate at least 300 degrees about the rotation axis 122 without substantial occlusion of the x-rays 112 by highly absorbing structures of the stage assembly 180.

Although commonly used terms are used to describe the systems and methods of certain implementations for ease of understanding, these terms are used herein to have their broadest reasonable interpretations. Although various aspects of the disclosure are described with regard to illustrative examples and implementations, the disclosed examples and implementations should not be construed as limiting. Conditional language, such as "can," "could," "might," or "may," unless specifically stated otherwise, or otherwise understood within the context as used, is generally intended to convey that certain implementations include, while other implementations do not include, certain features, elements, and/or steps. Thus, such conditional language is not generally intended to imply that features, elements, and/or steps are in any way required for one or more implementations. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

Conjunctive language such as the phrase "at least one of X, Y, and Z," unless specifically stated otherwise, is to be understood within the context used in general to convey that an item, term, etc. may be either X, Y, or Z. Thus, such conjunctive language is not generally intended to imply that certain implementations require the presence of at least one of X, at least one of Y, and at least one of Z.

Language of degree, as used herein, such as the terms "approximately," "about," "generally," and "substantially," represent a value, amount, or characteristic close to the stated value, amount, or characteristic that still performs a desired function or achieves a desired result. For example, the terms "approximately," "about," "generally," and "substantially" may refer to an amount that is within ±10% of, within ±5% of, within ±2% of, within ±1% of, or within ±0.1% of the stated amount. As another example, the terms "generally parallel" and "substantially parallel" refer to a value, amount, or characteristic that departs from exactly parallel by ±10 degrees, by ±5 degrees, by ±2 degrees, by ±1 degree, or by ±0.1 degree, and the terms "generally perpendicular" and "substantially perpendicular" refer to a value, amount, or characteristic that departs from exactly perpendicular by ±10 degrees, by ±5 degrees, by ±2 degrees, by ±1 degree, or by ±0.1 degree. The ranges disclosed herein also encompass any and all overlap, sub-ranges, and combinations thereof. Language such as "up to," "at least," "greater than," less than," "between," and the like includes the number recited. As used herein, the meaning of "a," "an," and "said" includes plural reference unless the context clearly dictates otherwise. While the structures and/or methods are discussed herein in terms of elements labeled by ordinal adjectives (e.g., first, second, etc.), the ordinal adjectives are used merely as labels to distinguish one element from another, and the ordinal adjectives are not used to denote an order of these elements or of their use.

Various configurations have been described above. It is to be appreciated that the implementations disclosed herein are not mutually exclusive and may be combined with one another in various arrangements. Although this invention has been described with reference to these specific configurations, the descriptions are intended to be illustrative of the invention and are not intended to be limiting. Various modifications and applications may occur to those skilled in the art without departing from the true spirit and scope of the invention. Thus, for example, in any method or process disclosed herein, the acts or operations making up the method/process may be performed in any suitable sequence and are not necessarily limited to any particular disclosed sequence. Features or elements from various implementations and examples discussed above may be combined with one another to produce alternative configurations compatible with implementations disclosed herein. Various aspects and advantages of the implementations have been described where appropriate. It is to be understood that not necessarily all such aspects or advantages may be achieved in accordance with any particular implementation. Thus, for example, it should be recognized that the various implementations may be carried out in a manner that achieves or optimizes one advantage or group of advantages as taught herein without necessarily achieving other aspects or advantages as may be taught or suggested herein.

What is claimed is:

1. An x-ray computed laminography imaging system configured to generate a transmission image of a region of interest of an object, the system comprising:
    a transmission x-ray source configured to generate x-rays at an x-ray source focal spot, at least some of the x-rays propagating along an x-ray propagation axis extending from the x-ray source focal spot through the region of interest of the object;
    a stage assembly comprising at least one rotation stage configured to rotate the object about a rotation axis extending through the region of interest, the rotation axis at an angle relative to a normal to the x-ray propagation axis in a range of 10 degrees to 60 degrees;
    at least one x-ray detector configured to intercept at least some of the x-rays propagating along the x-ray propagation axis, the at least one x-ray detector comprising at least one optical subsystem and a two-dimensional pixelated imaging circuitry comprising an imaging area configured to receive a two-dimensional image from the at least one optical subsystem, the at least one optical subsystem comprising:
        a scintillator having a surface normal and a thickness that are parallel to the x-ray propagation axis within ±10 degrees, the scintillator configured to generate visible light in response to x-rays impinging the scintillator; and
        at least one optical lens configured to receive the visible light from the scintillator and to focus the visible light into the two-dimensional image, the at least one optical lens having a depth of focus, the thickness of the scintillator in a range of 1 to 20 times the depth of focus.

2. The system of claim 1, wherein the thickness of the scintillator is in a range of 1 to 5 times the depth of focus.

3. The system of claim 1, wherein the at least one optical lens is configured to focus the two-dimensional image on the imaging area of the imaging circuitry.

4. The system of claim 1, wherein the at least one optical lens comprises an objective lens configured to receive at least a portion of the visible light from the scintillator and a tube lens configured to receive at least a portion of the visible light from the objective lens, the tube lens configured to focus the two-dimensional image on the imaging area of the imaging circuitry.

5. The system of claim 1, wherein the at least one optical subsystem comprises:
    a first optical subsystem comprising a first scintillator and at least one first optical lens configured to be translated into position to intercept the x-rays and to provide a first optical attribute for the two-dimensional image at the imaging area; and
    a second optical subsystem comprising a second scintillator and at least one second optical lens configured to be translated into position to intercept the x-rays and to provide a second optical attribute for the two-dimensional image at the imaging area, the second optical attribute different from the first optical attribute.

6. The system of claim 5, wherein the first and second optical attributes are optical magnifications.

7. The system of claim 5, wherein the first and second optical attributes are numerical apertures.

8. The system of claim 1, further comprising at least one linear translation stage configured to move the object relative to the rotation axis.

9. The system of claim 1, further comprising a gantry on which the x-ray source and the at least one x-ray detector are mounted, the gantry configured to rotate the x-ray source and the at least one x-ray detector about a rotation pivot point at an intersection of the x-ray propagation axis and the rotation axis.

10. The system of claim 9, wherein the gantry is configured to adjust an angle of the x-ray propagation axis relative to the rotation axis.

11. The system of claim 1, further comprising at least one source stage configured to translate the x-ray source relative to the object and relative to the at least one x-ray detector to adjust a magnification of the two-dimensional image relative to the region of interest.

12. The system of claim 11, wherein the at least one source stage is further configured to adjust an angle of the x-ray propagation axis relative to the rotation axis.

13. The system of claim 1, further comprising at least one detector stage configured to translate the at least one x-ray detector relative to the object and relative to the at least one x-ray source to adjust a magnification of the two-dimensional image relative to the region of interest.

14. The system of claim 13, wherein the at least one detector stage is further configured to adjust an angle of the x-ray propagation axis relative to the rotation axis.

15. The system of claim 1, wherein the at least one x-ray detector further comprises a second x-ray detector configured to be moved in place of the at least one optical subsystem and the two-dimensional pixelated imaging circuitry, such that the second x-ray detector receives the x-rays instead of the at least one optical subsystem and the two-dimensional pixelated imaging circuitry.

16. The system of claim 15, wherein the second x-ray detector is selected from a group consisting of: an energy discriminating flat panel detector, an amorphous selenium detector, and a photon counting detector.

17. The system of claim 1, wherein the stage assembly further comprises at least one linear translation stage mounted to the at least one rotation stage.

18. The system of claim 17, wherein the stage assembly further comprises a support configured to hold the object, the support having greater than 50% transmission to x-rays having x-ray energies greater than 50% of an acceleration voltage of the transmission x-ray source.

19. A method of generating at least one two-dimensional image of a region of interest of an object, the method comprising:
    emitting diverging x-rays from an x-ray source focal spot;
    propagating at least some of the x-rays along an x-ray propagation axis through the region of interest of the object;
    positioning the object at a plurality of rotational positions by rotating the object about a rotation axis extending through the region of interest, the rotation axis at an angle relative to a normal of the x-ray propagation axis in a range of 10 degrees to 60 degrees; and
    for one or more of the rotational positions of the object, detecting x-rays that have propagated through the region of interest, wherein said detecting comprises:
        impinging at least some of the x-rays that have propagated through the region of interest onto a scintillator having a surface normal and a thickness that are parallel to the x-ray propagation axis within ±10 degrees;
        guiding the visible light, using at least one optical lens or a magnifying fiber optic plate, at a two-dimensional pixelated imaging area of imaging circuitry; and
        generating, using the imaging circuitry, the two-dimensional image of the region of interest.

20. The method of claim 19, wherein said detecting further comprises moving a flat panel and/or photon counting detector in place of the scintillator and the at least one optical lens or a magnifying fiber optic plate and impinging at least some of the x-rays that have propagated through the region of interest onto the flat panel and/or photon counting detector.

21. The method of claim 19, wherein said detecting further comprises moving a second scintillator and a second at least one optical lens or a magnifying fiber optic plate in place of the scintillator and the at least one optical lens or a magnifying fiber optic plate and impinging at least some of the x-rays that have propagated through the region of interest onto the second scintillator, using the second scintillator to generate visible light in response to the x-rays impinging the second scintillator, and guiding the visible light, using the second optical assembly, at the two-dimensional pixelated imaging area of the imaging circuitry.

22. The method of claim 21, wherein the at least one optical lens or a magnifying fiber optic plate has a first depth of focus, the thickness of the scintillator in a range of 1 to 20 times the first depth of focus, and the second at least one optical lens or a magnifying fiber optic plate having a second depth of focus, a second thickness of the second scintillator equal to an integer multiple of the second depth of focus within ±10%, the second depth of focus different from the first depth of focus.

23. The method of claim 22, wherein the thickness of the scintillator is in a range of 1 to 5 times the first depth of focus.

* * * * *